United States Patent [19]

Askin et al.

[11] Patent Number: 5,728,840
[45] Date of Patent: Mar. 17, 1998

[54] PROCESS FOR MAKING AN EPOXIDE

[75] Inventors: David Askin, Warren; Kan K. Eng, Jersey City; Peter E. Maligres, Scotch Plains; Paul J. Reider; Kai Rossen, both of Westfield; Ralph P. Volante, Cranbury; Veena Upadhyay, Edison; Steven A. Weissman, Little Falls, all of N.J.

[73] Assignee: Merck & Co., Inc., Rahway, N.J.

[21] Appl. No.: 512,602

[22] Filed: Aug. 8, 1995

Related U.S. Application Data

[63] Continuation-in-part of Ser. No. 472,352, Jun. 7, 1995, abandoned, which is a continuation of Ser. No. 206,074, Mar. 4, 1994, abandoned.

[51] Int. Cl.$^6$ ............................................. C07D 263/52
[52] U.S. Cl. ............................................................. 548/217
[58] Field of Search ............................................... 548/217

[56] References Cited

U.S. PATENT DOCUMENTS 5,169,952  12/1992  Askin et al. ............................. 548/217
5,463,067  10/1995  Askin et al. ............................. 548/217

FOREIGN PATENT DOCUMENTS 0480714  4/1992  European Pat. Off. .
0491538  6/1992  European Pat. Off. .
0521686  1/1993  European Pat. Off. ............. 548/217
541168   5/1993  European Pat. Off. .
2270914  3/1994  United Kingdom .

OTHER PUBLICATIONS

Masuda, et al., J. Org. Chem. 1994, 59(19), 5550–5555.
Askin, et al., J. Org. Chem. 1992, 57(10), 2771–2773.
Tamaru, et al., J. Am. Chem. Soc., 1984, 104(4), 1079–1085.
Askin et al Tetrah. Lett. vol. 35 pp. 673–676 (Feb. 1994).

*Primary Examiner*—Donald G. Daus
*Attorney, Agent, or Firm*—Mary A. Appollina; Jack L. Tribble

[57] ABSTRACT

A process for synthesizing the epoxide of the formula

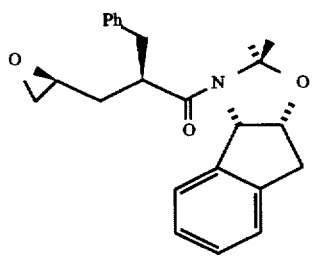

I

, consists of, at a minimum, formation of a halohydrin from the allyl acetonide reactat, followed by base-induced cyclization, the epoxide product I being useful as an intermediate for the synthesis of inhibitors of renin or HIV protease or other proteases.

13 Claims, No Drawings

PROCESS FOR MAKING AN EPOXIDE

BACKGROUND OF THE INVENTION

The present application is a continuation-in-part of Merck Case 19182CA, U.S. Ser. No. 08/472,352, filed Jun. 7, 1995, abandoned, which is a continuation of Merck Case 19182 U.S. Ser. No. 08/206,074 filed Mar. 4, 1994, now abandoned.

The present invention is concerned with a novel intermediate and process for synthesizing compounds which inhibit the protease encoded by human immunodeficiency virus (HIV), and in particular, the compound disclosed and referred to as "Compound J" in EPO 541,168 (U.S. Pat. No. 5,413,999, herein incorporated by reference), which published on May 12, 1993, or pharmaceutically acceptable salts thereof.

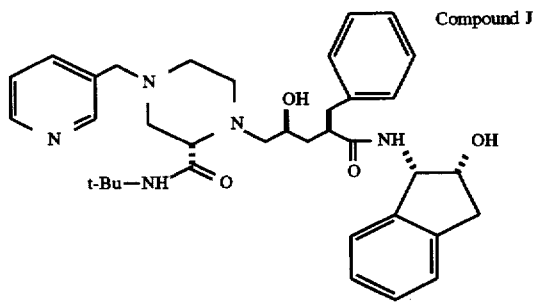

Compound J

These compounds are of value in the prevention of infection by HIV, the treatment of infection by HIV and the treatment of the resulting acquired immune deficiency syndrome (AIDS).

More specifically, the instant process involves the preparation of the epoxide intermediate for the production of Compound J, the HIV protease inhibitor depicted above. The process relates to iodohydrin formation of the allyl acetonide via the intermediate iodoiminolactone. Base-induced cyclization of the iodohydrin then forms the epoxide intermediate. The iodohydrin formation proceeds with high diastereoselectivity, and there is a substantial absence of hydrolysis of the amide bond linkage in this process.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including Compound J, that can be made from the novel intermediates and process of this invention are inhibitors of HIV protease, and are disclosed in EPO 541,168, which published on May 12, 1993.

Previously, the synthesis of Compound J and related compounds was accomplished via a 12-step procedure which employed a hydroxy protected dihydro-5(S)-hydroxymethyl-3(2H) furanone which was alkylated, and involved replacement of an alcohol leaving group on the alkylated furanone with a piperidine moiety. The coupled product was then hydrolyzed to open the furanone ring into a hydroxy acid moiety, and the acid was ultimately coupled to 2(R)-hydroxy-1(S)-aminoindane. This procedure is described in EPO 541,168. The extreme length of this route (12 steps), renders this process time consuming and labor intensive, and it requires the use of many expensive reagents and an expensive starting material. A route requiring fewer reaction steps and/or more efficient reagents would provide desirable economical and time-saving benefits.

The iodolactamization of olefinic tertiary amide A is known to occur with subsequent hydrolysis of the charged iodoiminolactam B intermediate giving the iodolactone C as the only isolated product (Scheme ALPHA). See Tamara, Y. et al., *J. Am. Chem. Soc.*, 106, 1079–1085 (1984); Trost, B. M. et al., eds. Comprehensive Organic Synthesis; Selectivity, Strategy, & Efficiency in Modern Organic Chemistry, Volume 4, Pergamon Press, New York 1991, p. 398–421. In this process, it is known that very efficient chirality transfer occurs from the 2-position to the 4-position, to give the 2,4-syn products (represented by the corresponding hydroxy-acid D) in high diastereoselectivity.

SCHEME ALPHA

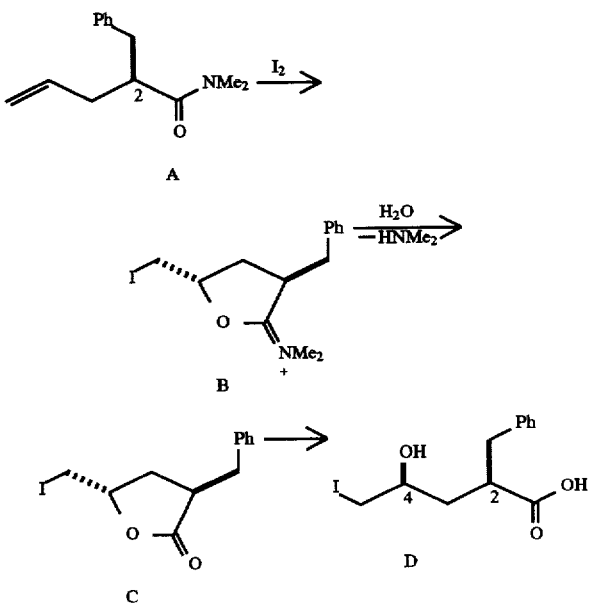

In another existing process, the acetonide is reacted with (S)-glycidyl rosylate in the presence of strong base LHMDS to form the epoxide (see Scheme BETA). Since both the starting material (S)-glycidyl tosylate and product are epoxides, the acetonide anion reacts also with the product epoxide; therefore, about 20% double addition byproducts after formed, in addition to the product epoxide in 71% yield. After crystallization from MeOH, an additional MTBE recrystallization was required to provide the epoxide free of dimer; consequently the overall isolated yield from the acetonide can range from 56–61%. The formation of double nucleophilic addition products is a problem inherent to the electrophile glycidyl rosylate. The (S)-glycidyl tosylate is also presently the most costly raw material in the synthesis of Compound J.

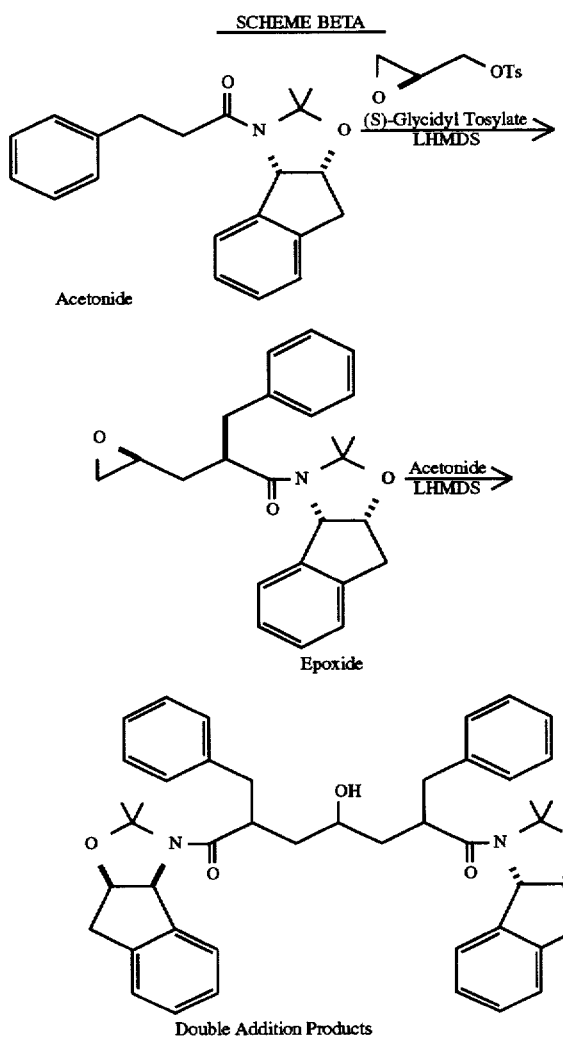

The reaction of the lithium enolate of the acetonide intermediate with electrophiles is known to occur with very high selectivity and in high yield for the desired 2(R) products. See Askin, D. et al., *J. Org. Chem.* 57, 2771–2773 (1992); Askin, D. et al., *Tetrahedron Lett.*, 35, 673–676 (1994). It was also known that halohydrin derivatives are cleanly converted to the desired epoxide intermediate for Compound J. It was however unexpected that the conditions of the instant invention would result in the isolation of the iodohydrin in excellent yield, exceeding 70% overall from the acetonide intermediates.

SUMMARY OF THE INVENTION

A process is disclosed for synthesizing the epoxide of the formula

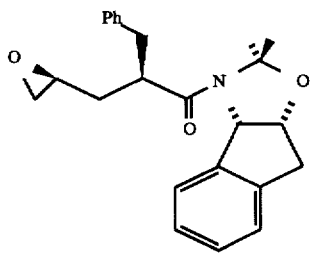

comprising the first step of formation of a halohydrin from the allyl acetonide reactant, followed by the step of base-induced cyclization. An additional first step involves allylation of an acetonide reactant to form the allyl acetonide. The products are useful as intermediates for the synthesis of inhibitors of renin or HIV protease or other proteases.

| ABBREVIATIONS | |
|---|---|
| Designation | |
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| Ts or tosyl or tosylate | p-toluenesulfonyl |
| Ns or nosyl or nosylate | 3-nitrobenzenesulfonyl |
| Tf or triflyl or triflate | trifluoromethanesulfonyl |
| Ms or mesyl or mesylate | methanesulfonyl |
| | Coupling Reagent |
| BOP reagent | benzotriazol-1-yloxytris(dimethylamino)-phosphonium hexafluorophosphate |
| BOP-Cl | bis(2-oxo-3-oxazolidinyl)phosphinic chloride |
| EDC | 1-ethyl-3-(3-dimethylaminopropyl) carbodiimide hydrochloride |
| | Other |
| BOC-ON | 2-(tert-butylcarbonyloxyimino)-2-phenylacetonitrile |
| (BOC)$_2$O (BOC$_2$O or Boc$_2$O) | di-t-butyl dicarbonate |
| n-Bu$_4$N$^+$F$^-$ | tetrabutyl ammonium fluoride |
| nBuLi (n-BuLi) | n-butyllithium |
| (S)-CSA | (1S)-(+)-10-camphorsulfonic acid |
| DABCO | diazabicyclooctane |
| DBN | diazabicyclononane |
| DBU | diazabicyloundecane |
| DI | deionized |
| DIEA or DIPEA | diisopropylethylamine |
| DMA | dimethylacetamide |
| DMAP | dimethylaminopyridine |
| DME | dimethoxyethane |
| DMF | dimethylformamide |
| DMPU | dimethyltetrahydropyrimidinone |
| DMSO | dimethylsulfoxide |
| Et$_3$N | triethylamine |
| EtOAc | ethyl acetate |
| h | hour(s) |
| IPA | 2-propanol |
| KF | Karl Fisher titration for water |
| LDA | lithium diisopropylamide |
| LHMDS | lithium hexamethyldisilazide |
| L-PGA | (L)-pyroglutamic acid |
| MeCN | acetonitrile |
| MTBE | methyl t-butyl ether |
| NMP | N-methylpyrrolidinone |
| r.t. | room temperature |
| TFA | trifluoroacetic acid |
| TG | thermal gravimetry: loss on heating |
| THF | tetrahydrofuran |
| TLC | thin layer chromatography |

| ABBREVIATIONS | |
|---|---|
| Designation | |
| TMEDA | tetramethylethylenediamine |
| TMU | tetramethyl urea |

DETAILED DESCRIPTION OF THE INVENTION

The process of the present invention is illustrated by the following Scheme:

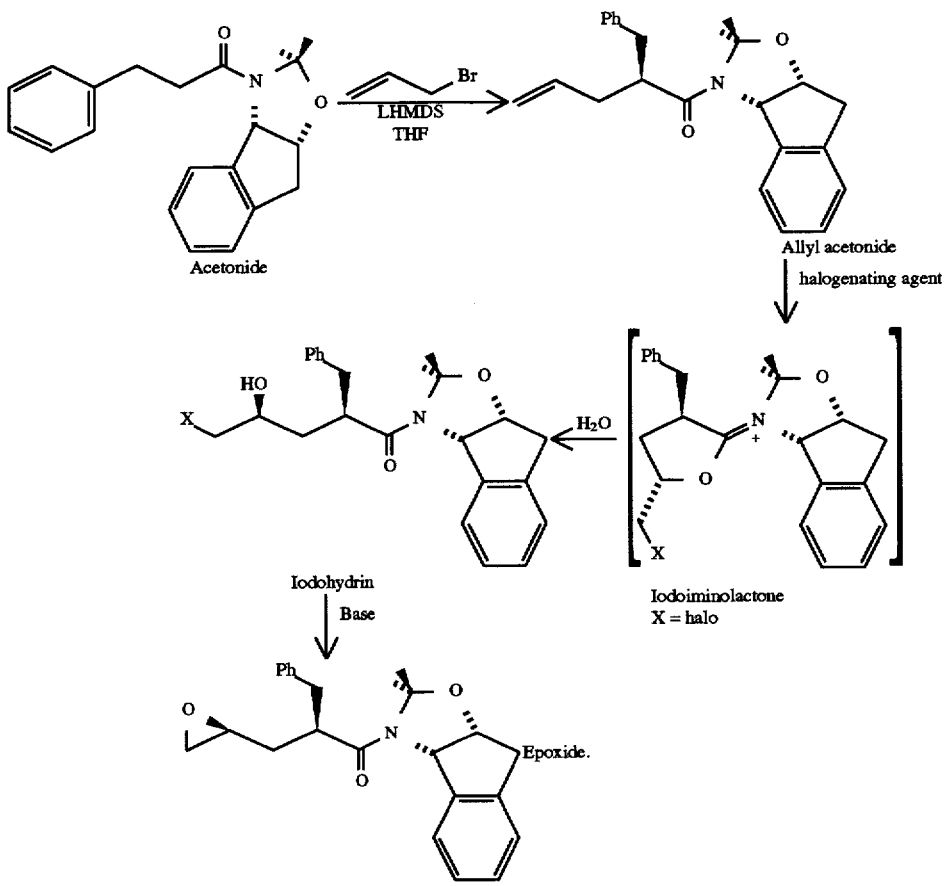

The above scheme illustrates three steps, beginning with allylation of the acetonide, followed by halohydrin formation, and then base-induced cyclization forming product epoxide.

In the present invention, a process of synthesizing the epoxide of formula I,

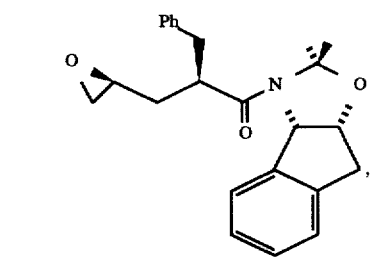

comprises the steps of:

(a) contacting one equivalent of the allyl acetonide of formula II,

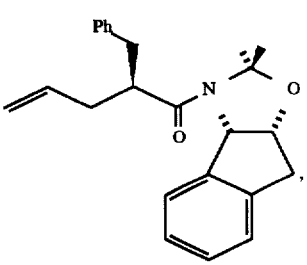

with about one to two equivalents of a halogenating agent in solvent mixed with aqueous weak base, at a temperature range of between about −40° C. and about 100° C., to form the halohydrin of formula III, and

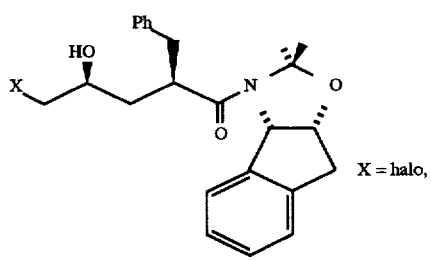

III

X = halo, (b) adding base in solvent or solvents to elicit the formation of the epoxide of formula I.

From the acetonide reactant the present process of synthesizing the epoxide of formula I,

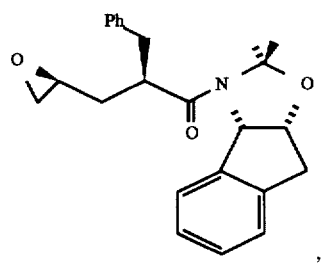

I comprises the steps of:

(a) reacting one equivalent of the acetonide

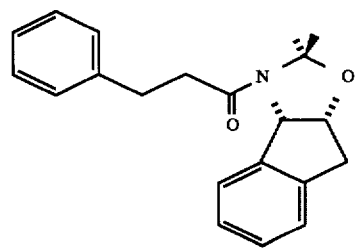

with about one equivalent of allylhalide in strong base, to give the allyl acetonide of formula II,

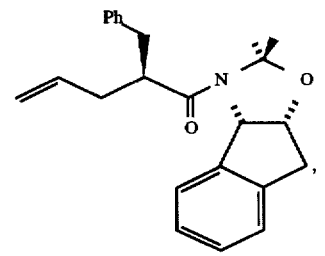

II (b) mixing thereto about one to two equivalents of a halogenating agent in solvent mixed with aqueous weak base, at a temperature range of between about −40° C. and about 100° C., to form the halohydrin of formula III, and

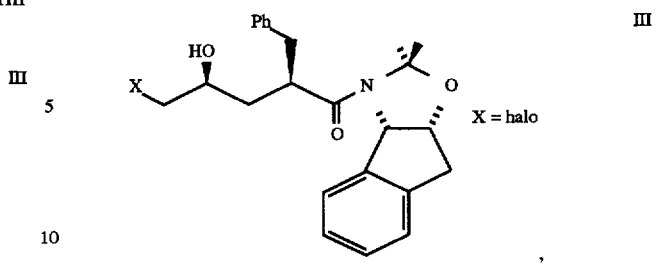

III

X = halo (c) adding base in solvent or solvents, to elicit formation of the epoxide of formula I.

In the preparation of the allyl acetonide of Scheme GAMMA, the preferred allylation reagents include allyl halides such as allyl chloride, allyl bromide or allyl iodide, as well as other allyl electrophiles such as allyl methane sulfonate or allyl esters in the presence of a transition metal catalyst. Most preferred allylation reagents include allyl halides such as allyl chloride, allyl bromide, and allyl iodide.

For this allylation reaction, preferred bases are strong bases and include amide bases such as the lithium, sodium, potassium or magnesium salts of amines, such as diethylamine, disopropylamine, dicyclohexylamine, piperidine, pyrrolidine, or bistrimethylsilylamine; metal alkyls such as the $C_{1-6}$ alkyllithium such as n-, iso-, sec-, and tert-butyllithium, methyl, ethyl, or aryl lithiums such as phenyllithium; Grignard reagents such as methyl ethyl, propyl, or butyl magnesium halide; alkoxides such as the methoxide, ethoxide, isopropoxide, tert-butoxide, tert-amyloxide alkoxides of lithium, sodium, potassium or magnesium.

In the allylation reaction, the most preferred base is lithium hexamethyldisilazide (LHMDS).

Also in the allylation reaction, preferred solvents include ethereal solvents such as THF, DME, MTBE, diethylether, diglyme, or dibutylether; hydrocarbon solvents such as pentane, hexane, heptane, benzene, toluene or ethyl benzene; or other solvents compatible with bases and organo-metallic reagents such as DMSO, DMPU, NMP, TMU, TMEDA, and crown ethers; and including mixtures of these solvents.

Most preferred solvents for allylation are ethereal solvents for allylation such as THF, DME, and MTBE.

The preferred temperature range for the allylation is −78° C. to +30° C. The incubation period lasts at least 15 minutes and typically up to 3 hours.

For halohydrin formation, preferred halogenating reagents include halogens, interhalogen compounds, halonium salts, or hypohalite salts or esters, oxyhalogen salts or acids, halo-amides, halo-ureas, halo-carbamates, halo-hydantoins, halo-sulfonamides, halo-amines, or other halogenated nitrogen compounds, or combinations thereof with either halide salts or phase transfer catalysts or both. Preferred halogenating reagents are hypohalite salts or esters, halo amides, ureas, carbamates, sulfonamides, amines, or other halogenated nitrogen compounds such as N-iodosuccinimide, N-bromosuccinimide with an iodide salt, or N-chlorosuccinimide with an iodide salt, 1,3-dichloro-5,5-dimethylhydantoin with an iodide salt, or iodine. Most preferred halogenating reagents are N-iodosuccinimide, N-bromosuccinimide in combination with an iodide salt, or N-chlorosuccinimide in combination with an iodide salt, 1,3-dichloro-5,5-dimethylhydantoin with an iodide salt, or iodine.

Reaction conditions for halohydrin formation are solutions, suspensions, or other biphasic systems containing weak bases such as sodium bicarbonate, calcium carbonate, magnesium hydroxide, basic alumina, neutral alumina, sodium acetate, dibasic sodium phosphate, dibasic potassium phosphate, potassium fluoride, other salts, or water in common organic solvents. Preferred reaction conditions are weak bases such as sodium bicarbonate, basic alumina, potassium fluoride, or water. Most preferred reaction conditions are basic alumina, or sodium bicarbonae. Solvents must be compatible with the reaction conditions and include ethers, aromatic chlorinated hydrocarbons, esters, alcohols, MeCN, DMF, DMPU, or ketones. Preferred are chlorinated hydrocarbons, ethers and esters. Most preferred are dichloromethane, IPAC, THF, EtOAc, DME, and MTBE. Temperature range is between about −40° C. and about 100° C., but preferably between about 0 and about 35° C. Incubation lasts at least about 10 minutes and is typically stopped before about 48 hours.

Base-induced cyclization to form the epoxide is accomplished by treating the halohydrin with a base. Preferred bases for such cyclization include hydroxides and oxides of lithium, sodium, potassium, magnesium, calcium, or tetraalkylammonium; alkoxides such as lithium, sodium, potassium, magnesium, and tetraalkylammonium methoxide, ethoxide, n- and iso-propoxide, n-, iso-, sec-, and tert-butoxide. Other suitable bases include tertiary and hindered amines such as tfiethylamine, DIEA, DBU, DBN, DABCO, methyl morpholine, diisiopropylamine, dicyclohexyl amine, bis trimethyl-silylamine or tetramethylpiperidine as well as metal aide salts thereof. Most preferred bases are lithium, sodium, potassium, or tetraalkylammonium hydroxides; alkoxides such as lithium, sodium and potassium methoxide, ethoxide, iso-propoxide, or tert-butoxide; or tertiary mines such as DIEA. Alkali hydroxide means LiOH, KOH, or NaOH or mixtures thereof.

Also for the base-induced cyclization, preferred solvents are ethers, esters, hydrocarbons, aromatic solvents, chlorinated hydrocarbons, ketones, water, alcohols, DMSO, MECN, DMF, or DMPU, or other polar solvents, or mixtures thereof. Most preferred solvents are ethers, esters, alcohols, or polar aprotic solvents.

Base-induced cyclization is carried out in a temperature range of between about −40° C. and about 100° C. Incubation lasts at least about 10 minutes and is typically stopped before about 48 hours.

In the process of the present invention, a wide variety of solvents can be used, except where noted. Hydrocarbon solvents include pentane, hexane, heptane, cyclohexane, methyl-cyclohexane, benzene, toluene and xylene. Aromatics as solvents include benzene, toluene, xylene, and ethylbenzene. Chlorinated hydrocarbons as solvents include methylene chloride, chloroform, carbontetrachloride, dichloroethane, trichloroethane, tetrachloroethane, trichloroethylene, tetrachloroethylene, chlorobenzene and dichlorobenzene. Ethers as solvents include diethyl ether, dibutylether, tetrahydrofuran, dimethoxyethane, diethoxyethane, and MTBE. Esters as solvents include ethyl acetate, IPAC, and ethoxyethyl acetate. Ketones as solvents include acetone, MEK, and MIBK. Alcohols as solvents include methanol, ethanol, propanol, isopropanol, butanol, and methhoxyethanol. Polar aprotic solvents as solvents include DMF, DMA, DMSO, DMPU, TMU, NMP and acetonitrile. Tertiary amines as solvents include triethylamine, diisopropyl ethyl amine, pyridine, DABCO, DBU, DBN, penamethyl piperidine, and DMAP.

In one embodiment of the present invention, a process of synthesizing the epoxide of formula I,

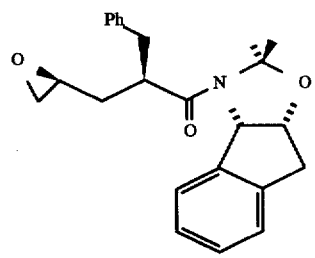

comprises the steps of:

(a) contacting one equivalent of the allyl acetonide of formula II,

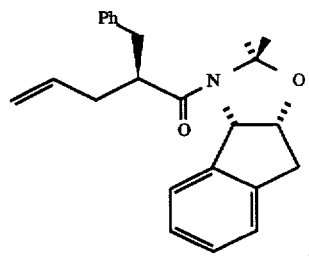

with about one to two equivalents of a halogenating agent, in solvent mixed with aqueous weak base, at a temperature range of between about −40° C. and about 100° C., to form the halohydrin of formula III,

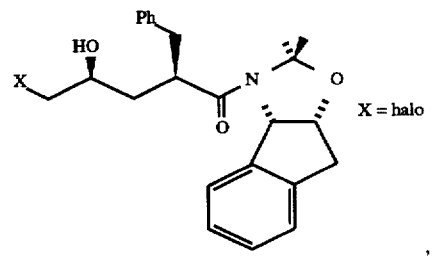

said halogenating agent selected from the group consisting of iodine, N-iodosuccinimide, N-bromosuccinimide, N-chlorosuccinimide or 1,3-dichloro-5,5-dimethylhydantoin, the last three of which may be combined with an iodide salt, said solvent selected from the group consisting of dichloromethane, IPAC, THF, EtOAc, DME, and MTBE, said weak base selected from basic alumina or sodium bicarbonate, and (b) adding base in water to elicit formation of the epoxide of formula I, said base selected from the group consisting of lithium hydroxide, sodium hydroxide, potassium hydroxide, tetralkylammonium hydroxide; any $C_{1-4}$ alkoxide of lithium, sodium or potassium; and DIEA.

In another embodiment of the present invention involving the acetonide reactant, the present process of synthesizing the epoxide of formula I, comprises the steps of:

(a) reacting one equivalent of the acetonide

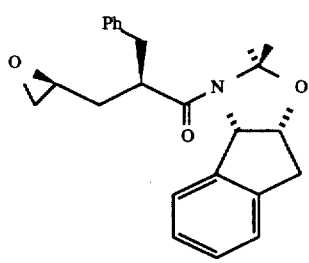

with about one equivalent of allylhalide in strong base, said allyl halide selected from allyl chloride, allyl bromide and allyl iodide, to give the allyl acetonide of formula II,

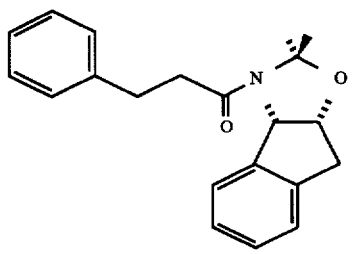

(b) mixing thereto about one to two equivalents of a halogenating agent in solvent mixed with aqueous weak base, at a temperature range of between about −40° C. and about 100° C., to form the halohydrin of formula III,

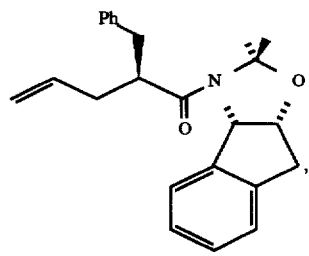

said halogenating agent selected from the group consisting of iodine, N-iodosuccinimide, N-bromosuccinimide, N-chlorosuccinimide or 1,3-dichloro-5,5-dimethylhydantoin, the last three of which may be combined with an iodide salt, said solvent selected from the group consisting of dichloromethane, IPAC, THF, EtOAc, DME, and MTBE, said weak base selected from basic alumina or sodium bicarbonate, and (c) adding base in water to elicit formation of the epoxide of formula I, said base selected from the group consisting of lithium hydroxide, sodium hydroxide, potassium hydroxide, tetralkylammonium hydroxide; any $C_{1-4}$ alkoxide of lithium, sodium or potassium; and DIEA.

In another embodiment of the present invention, a process of synthesizing the epoxide of formula I,

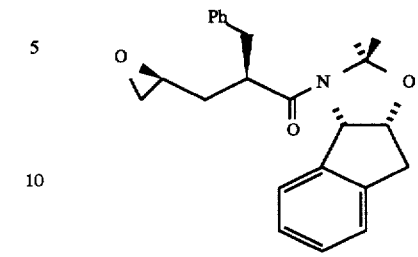

comprises the steps of:

(a) contacting one equivalent of the allyl acetonide of formula II,

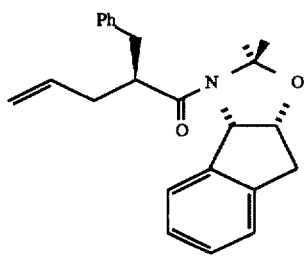

said allyl acetonide dissolved in isopropyl acetate, with about one to two equivalents of N-iodosuccinimide in about 0.5M aqueous sodium bicarbonate, at room temperature, to form the iodohydrin of formula III, and

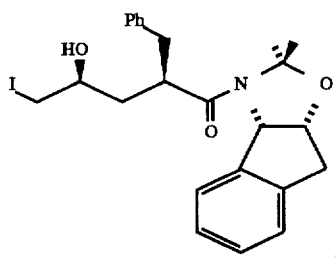

(b) adding alkali hydoxide in water to elicit formation of the epoxide of formula I.

In another embodiment of the present invention, the process of synthesizing the epoxide of formula I,

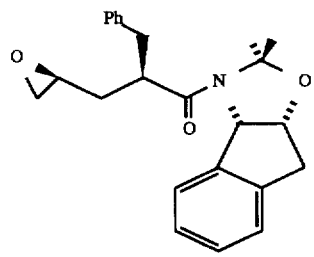

comprises the steps of:

(a) reacting one equivalent of the acetonide

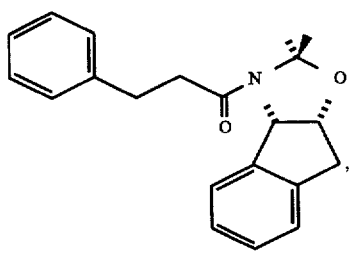

said acetonide dissolved in ethereal solvent, with about one equivalent of allylbromide and about one equivalent of about 1.0–2.0M lithiumhexamethyldisilazide (in ethereal solvent), to give the allyl acetonide of formula II,

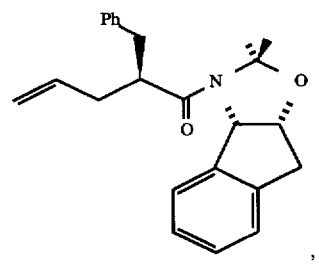
II (b) mixing thereto about one to two equivalents of N-iodosuccinimide in about 0.5M aqueous sodium bicarbonate, at room temperature, to form the iodohydrin of formula III, and

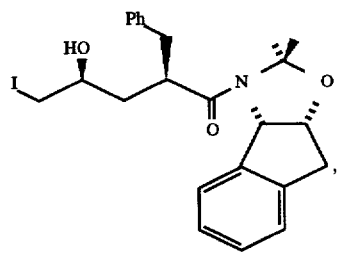
III (c) adding alkali hydroxide in water to elicit formation of the epoxide of formula I.

In another embodiment of the present invention, the process of synthesizing the epoxide of formula I,

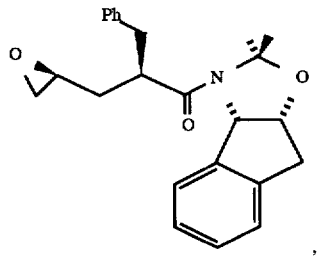
I comprises the steps of:

(a) contacting one equivalent of the allyl acetonide of formula II,

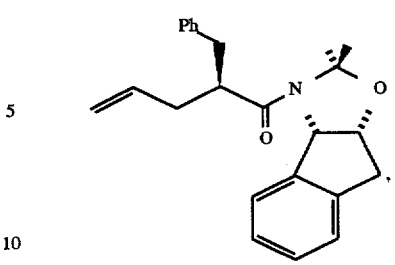
II said allyl acetonide dissolved in isopropyl acetate, with aqueous sodium bicarbonate solution and between about 0.5 and about 1.0 equivalents of 1,3-dichloro-5,5-dimethylhydantoin;

(b) cooling the resulting mixture to between about 5 °C. and about 10° C.;

(c) adding thereto excess aqueous sodium iodide, warming the reaction mixture to between about 21° C. and about 25° C., and thereafter aging the reaction mixture for between about 1 hour and about 8 hours;

(d) quenching by adding aqueous sodium sulfite, to form the iodohydrin of formula III, and

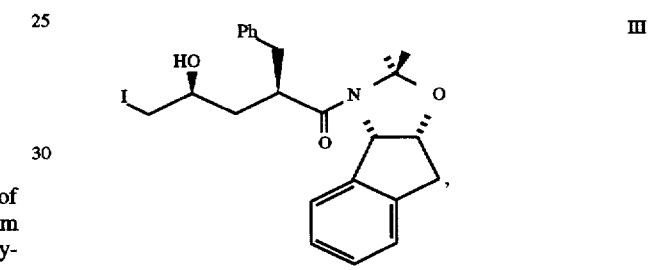
III (e) adding sodium methoxide in methanol to elicit formation of the epoxide of formula I.

In another embodiment of the present invention, the process of synthesizing the epoxide of formula I,

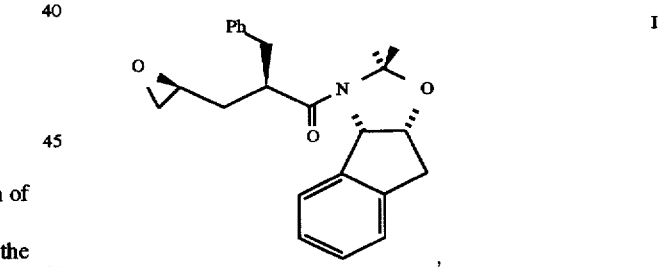
I comprises the steps of:

(a) reacting one equivalent of the acetonide

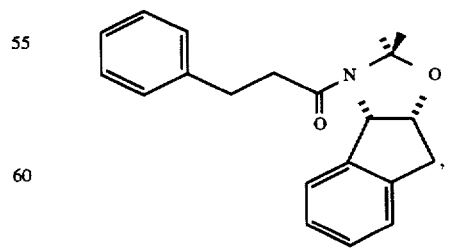

said acetonide dissolved in ethereal solvent, with about one equivalent of allylbromide and about one equivalent of about 1.0–2.0M lithiumhexamethyldisilazide (in ethereal solvent), at a temperature of between about −10° C. and about −20° C., to give the allyl acetonide of formula II,

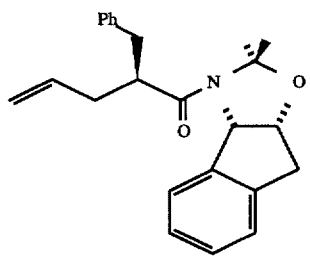

(b) quenching with citric acid;

(c) contacting the allyl acetonide product of step (b), said allyl acetonide dissolved in isopropyl acetate, with aqueous sodium bicarbonate solution and between about 0.5 and about 1.0 equivalents of 1,3-dichloro-5,5-dimethylhydantoin;

(d) cooling the resulting mixture to between about 5° C. and about 10° C.;

(e) adding thereto excess aqueous sodium iodide, warming the reaction mixture to between about 21° C. and about 25° C., and aging between about 1 hour and about 8 hours;

(f) quenching by adding aqueous sodium sulfite; to form the iodohydrin of formula III, and

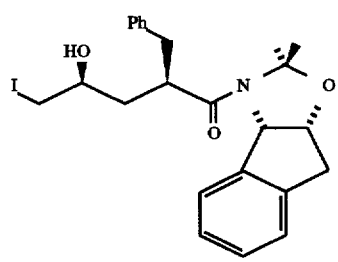

(g) adding sodium methoxide in methanol to elicit formation of the epoxide of formula I.

In another embodiment of the same invention, the process of synthesizing the epoxide of formula I,

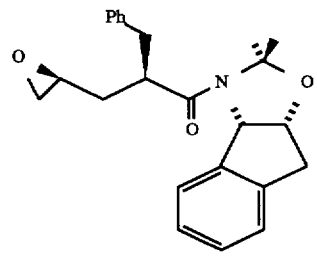

comprises the steps of:

(a) contacting one equivalent of the allyl acetonide of formula II,

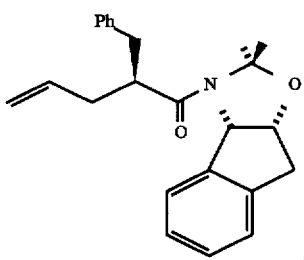

said allyl acetonide dissolved in THF, with aqueous sodium bicarbonate solution and excess iodine;

(b) aging the resulting mixture for between about 3 hours and about 8 hours;

(c) quenching by adding aqueous sodium sulfite, to give

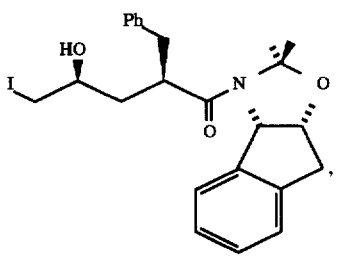

(d) adding sodium methoxide in methanol to elicit formation of the epoxide of formula I.

In another embodiment of the same invention, the process of synthesizing the epoxide of formula I,

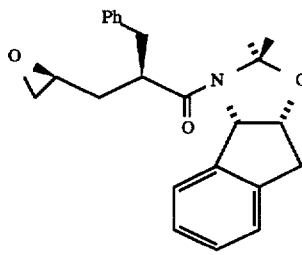

comprises the steps of:

(a) reacting one equivalent of the acetonide

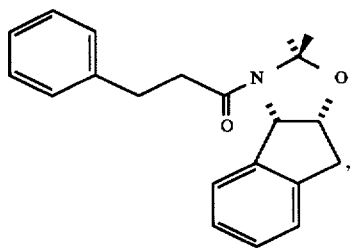

said acetonide dissolved in ethereal solvent, with about one equivalent of allylbromide and about one equivalent of about 1.0–2.0M lithiumhexamethyldisilazide (in ethereal solvent), at a temperature of between about −10° C. and about −20° C., to give the allyl acetonide of formula II,

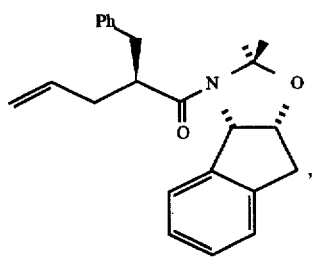

(b) quenching with citric acid;

(c) contacting the allyl acetonide product of step (b), said allyl acetonide dissolved in THF, with aqueous sodium bicarbonate solution and excess iodine;

(d) aging the resulting mixture for between about hours and about 8 hours;

(e) quenching by adding aqueous sodium sulfite, to give

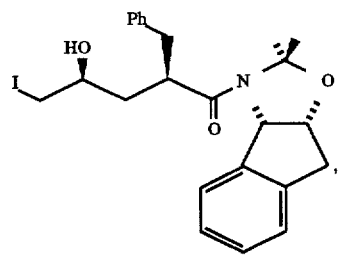

(f) adding sodium methoxide in methanol to elicit formation of the epoxide of formula I.

In another embodiment of the present invention, the process of synthesizing the epoxide of formula I,

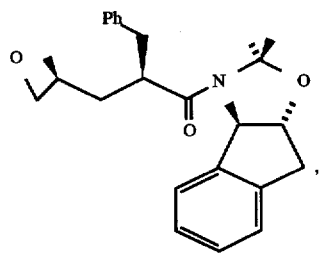

comprises the steps of:
(a) contacting one equivalent of the allyl acetonide of formula II,

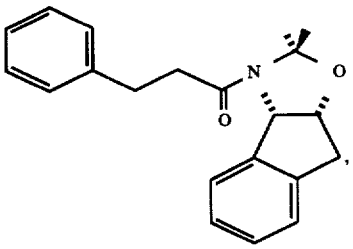

said allyl acetonide dissolved in isopropyl acetate, with aqueous sodium bicarbonate solution and between about 1.0 and about 2.0 equivalents of N-chlorosuccinimide;

(b) cooling the resulting mixture to between about 5° C. and about 10° C.;

(c) adding thereto excess aqueous sodium iodide, warming the reaction mixture to between about 21° C. and about 25° C., and thereafter aging the reaction mixture for between about 1 hour and about 8 hours;

(d) quenching by adding aqueous sodium sulfite, to form the iodohydrin of formula III, and

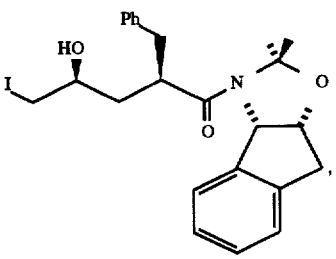

(e) adding sodium methoxide in methanol to elicit formation of the epoxide of formula I.

In another embodiment of the present invention, the process of synthesizing the epoxide of formula I,

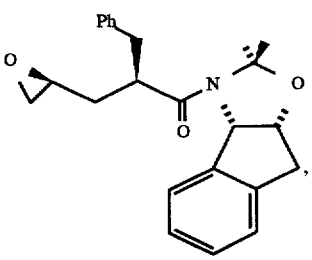

comprises the steps of:
(a) reacting one equivalent of the acetonide

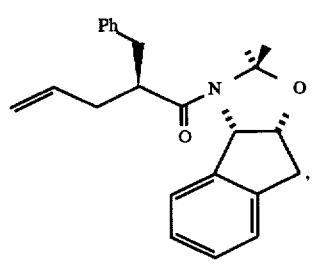

said acetonide dissolved in ethereal solvent, with about one equivalent of all ylbromi de and about one equivalent of about 1.0-2.0M lithiumhexamethyldisilazide (in ethereal solvent), at a temperature of between about -10° C. and about -20° C., to give the allyl acetonide of formula II,

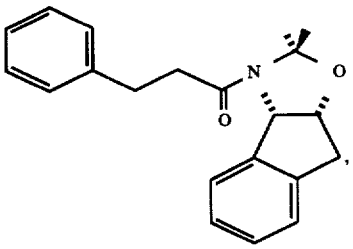

(b) quenching with citric acid;

(c) contacting the allyl acetonide product of step (b), said allyl acetonide dissolved in isopropyl acetate, with aqueous sodium bicarbonate solution and between about 1.0 and about 2.0 equivalents of N-chlorosuccinimide;

(d) cooling the resulting mixture to between about 5° C. and about 10° C.;

19

(e) adding thereto excess aqueous sodium iodide, warming the reaction mixture to between about 21° C. and about 25° C., and aging between about 1 hour and about 8 hours;

(f) quenching by adding aqueous sodium sulfite; to form the iodohydrin of formula III, and

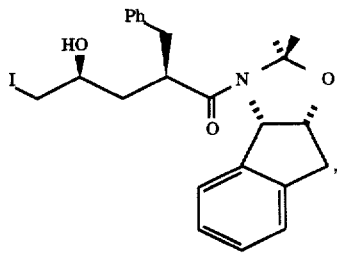

III (g) adding sodium methoxide in methanol to elicit formation of the epoxide of formula I.

The processes and intermediates of this invention are useful for the preparation of end-product compounds that are useful in the inhibition of HIV protease, the prevention or treatment of infection by the human immunodeficiency virus (HIV) and the treatment of consequent pathological conditions such as AIDS. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus the end-product compounds that are made from the processes and intermediates of this invention are commercial products to be sold for these purposes.

HIV protease inhibitor compounds that can be made from the intermediates, and proce. sses of the instant invention are disclosed in EPO 541,168 (U.S. Pat. No. 5,413,999). The HIV protease inhibitory compounds may be administered to patients in need of such treatment in pharmaceutical compositions comprising a pharmaceutical carder and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included int he present invention.

When any variable (e.g., aryl, heterocycle, R, $R^1$, $R^2$, n, X, etc.) occurs more than one time in any constituent, its definition on each occurrence is independent of its definition at every other occurrence. Also, combinations of substituents and/or variables are permissible only if such combinations result in stable compounds.

20

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl); "Halo", as used herein, means fluoro, chloro, bromo and iodo. As used herein, "aryl" is intended to mean phenyl (Ph) or naphthyl.

Representative experimental procedures utilizing the novel process are detailed below. These procedures are exemplary only and should not be construed as being limitations on the novel process of this invention.

EXAMPLE 1

Conversion of Acetonide to Allyl Acetonide

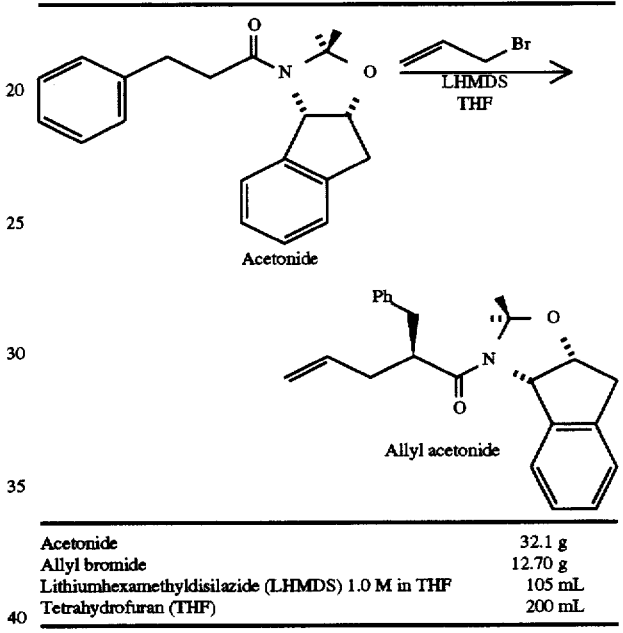

| Acetonide | 32.1 g |
|---|---|
| Allyl bromide | 12.70 g |
| Lithiumhexamethyldisilazide (LHMDS) 1.0 M in THF | 105 mL |
| Tetrahydrofuran (THF) | 200 mL |

The acetonide was dissolved in 200 mL THF in a 100 mL 3 neck flask equipped with an addition funnel and degassed by bubbling in nitrogen for 20 min. The mixture was cooled to −25° C. and the allyl bromide was added via a weighed syringe. The LHMDS was transferred to the addition funnel under nitrogen pressure via cannula. The LHMDS was allowed to slowly drop into the magnetically stirred reaction mixture over 20 min. The internal temperature reached −14° C. while the cooling bath was at −30° C. The mixture was aged at −20° to −15° C. for 30 min. Water (100 mL) and IPAC (100 mL) were added and the temperature rose to 5° C. The lower aqueous phase was discarded and the organic phase was washed with 100 mL of 0.2M HCl in 3% aq. NaCl, 30 mL brine, and 30 mL 0.5M sodium bicarbonate. The organic phase was evaporated (55° C., 100 Torr) to an oil, another 40 mL of IPAC were added, and the mixture was again evaporated to an oil. At this point the crude allyl acetonide may be taken directly on to the next step or purified by crystallization from 30:1 hexane-IPAC or 30:1 methylcyclohexane-IPAC to give the allyl acetonide as a white crystalline solid in 87% yield.

Allyl acetonide $^{13}$C NMR data for major rotamer (62.5 MHz)

| | | | |
|---|---|---|---|
| 171.0 | 140.4 | 140.2 | 134.8 |
| 129.6 | 128.6 | 128.2 | 127.1 |
| 126.6 | 125.6 | 124.0 | 117.9 |
| 96.8 | 78.9 | | |
| | 65.6 | 47.5 | 38.6 |
| 38.0 | 36.1 | 26.6 | 24.1 ppm |

EXAMPLE 2

Conversion of AIM Acetonide to Iodohydrin with NIS and Cyclization to Epoxide

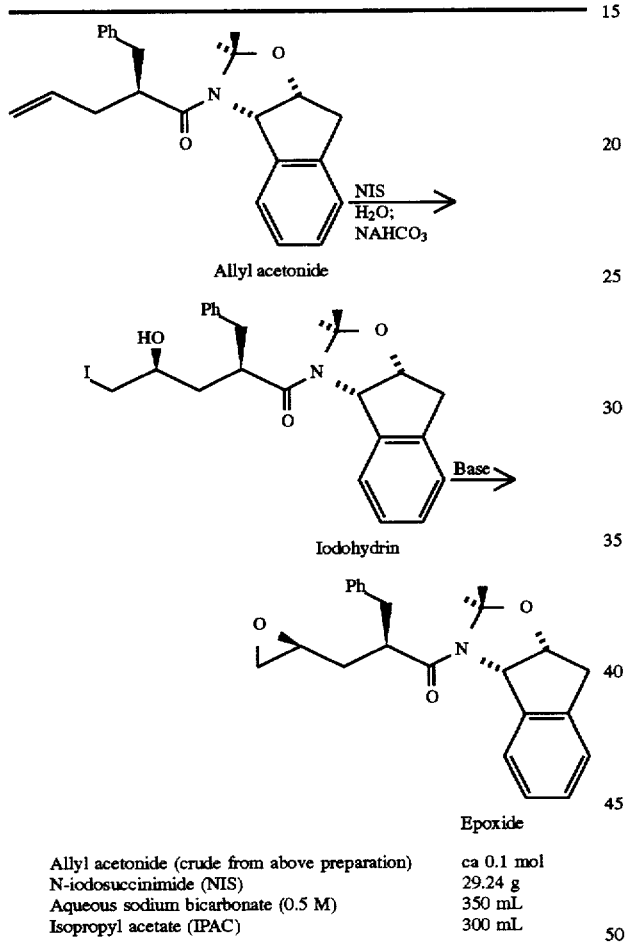

| | |
|---|---|
| Allyl acetonide (crude from above preparation) | ca 0.1 mol |
| N-iodosuccinimide (NIS) | 29.24 g |
| Aqueous sodium bicarbonate (0.5 M) | 350 mL |
| Isopropyl acetate (IPAC) | 300 mL |

The crude allyl acetonide was dissolved in IPAC and stirred with the aqueous sodium bicarbonate and NIS for 17 h. Aqueous sodium bisulfite (38–40%) solution was added and the upper organic phase was separated. The organic phase was washed with 300 mL water and 2×100 mL brine. At this point the crude iodohydrin solution in IPAC can be directly taken on to the next step or the solution could be evaporated and crystallized from methylcyclohexane-IPAC to give the iodohydrin as a pale yellow crystalline solid. $^{13}C$ NMR of Iodohydrin, data for major rotamer (62.5 MHz):

| | | | |
|---|---|---|---|
| 172.2 | 140.6 | 140.4 | 139.3 |
| 129.5 | 128.8 | 128.2 | 127.2 |
| 126.8 | 125.7 | 124.0 | 96.9 |
| 79.1 | 68.7 | 65.8 | 43.7 |
| 40.6 | 39.0 | 36.2 | 26.5 |
| 24.3 | 16.3 ppm | | |

| | |
|---|---|
| Iodohydrin (IPAC solution crude from above preparation) | ca 0.1 mol |
| Lithium hydroxide monohydrate | 50 g |
| Water | 200 mL |

The iodohydrin in IPAC was stirred with the lithium hydroxide in water for 3 h at 25°–30° C. The upper organic phase was washed with 200 mL water and 200 mL brine and was dried over ca 2 g of magnesium sulfate. The IPAC solution was filtered and evaporated (50°–60° C., 100 Torr) down to ca 50 mL when the epoxide began to crystallize. The mixture was allowed to cool to 25° C. over 30 min and 75 mL of methylcyclohexane were added in 10 mL portions with stirring over 30 min. The mixture was aged for 1 h and the crystals were filtered off and washed with 2×20 mL methylcyclohexane and dried to give 24.10 g (64%) of the epoxide as a white crystalline solid of 99.9 A% purity by HPLC. The mother liquor and washes were evaporated to an oil and dissolved in 40 mL IPAC. The solution was treated with 10 g of Darco G60 carbon for 2 h at 25° C. and filtered through a pad of Solkafloc. The flitrate was evaporated down to ca 20 mL and 40 mL of methylcyclohexane were added. The crystalline epoxide was filtered off and washed with 2×10 mL methylcyclohexane to afford another 4.96 g (13%) of epoxide 96.2 A % by HPLC. The conversion of the iodohydrin to epoxide may also be accomplished by the addition of 1.7M potassium-tert-butoxide in THF (0.70 mL, 1.2 mmol) or 5M potassium hydroxide in methanol (0.24 mL, 1.2 mmol) or DIEA (155 rag, 1.2 mmol) to a solution of the iodohydrin (505 mg, 1.0 mmol) in IPAC (2–3 mL) followed by washing with 2×2 mL water and crystallization from methylcyclohexane-IPAC.

EXAMPLE 3

A. Conversion of Allyl Acetonide to Iodohydrin with NCS/NaI

| | |
|---|---|
| Allyl acetonide | 26.15 g |
| N-chlorosuccinamide (NCS) | 22.7 g |
| Sodium iodide | 25.5 g |
| Aqueous sodium bicarbonate (0.5 M) | 350 mL |
| Isopropyl acetate (IPAC) | 300 mL |

The NCS and NaI were stirred together in 200 mL of water for 20 min. The mixture turned dark brown then immediately a black solid separated out. The solid dissolved and the color faded to clear yellow with further aging. The crude allyl acetonide was dissolved in IPAC and stirred with the aqueous sodium bicarbonate and the clear yellow solution prepared above for 17 h. Aqueous sodium bisulfite (38–40%) solution was added and the upper organic phase was separated. The organic phase was washed with 300 mL water and 2× 100 mL brine. At this point the crude iodohydrin solution in IPAC can be directly taken on to the next step or the solution could be evaporated and crystallized from methylcyclohexane-IPAC to give the iodohydrin as a pale yellow crystalline solid.

B. Conversion of Allyl Acetonide to Iodohydrin with 1,3-dichloro-5,5-dimethylhydantoin (DCDMH)/NaI

| | |
|---|---|
| Allyl acetonide | 38.5 g in 300 mL solution |
| 1,3-dichloro-5,5-dimethylhydantoin (DCDMH) | 17.8 g |
| Sodium iodide | 27.2 g |
| Aqueous sodium bicarbonate | 6.25 g in 172 ml water |

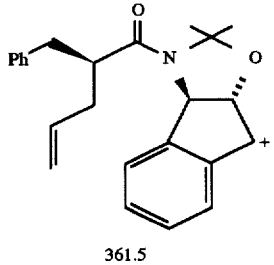

361.5

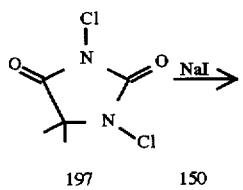

197  150

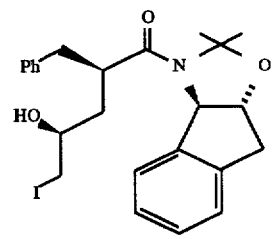

505.4

At RT, a solution of allyl acetonide (38.46 assay g; 300 ml solution @128.2 g/l; 106 mmols) in IpAC was charged to a 1-liter Morton flask followed by an aqueous sodium bicarbonate solution (6.25 g in 172 ml water; 75 mmols) and the dicholorodimethylhydatoin (17.8 g; 90.4 mmols). The resulting reaction mixture was cooled to 5.5° C. and aqueous sodium iodide (27.2 g in 21 ml water; 181 mmols) was added dropwise over 18 min. during which time the reaction temp did not exceed 9.2° C. The batch was then warmed to 24°–25° C. over 25 min and aged for 2 hrs. Assay of the reaction mixture showed >99.0% conversion. Aqueous sodium sulfite (16 g in 64 ml water; 127 mmols) was added dropwise over 5 min. during which time the reaction temp. rose to a maximum of 27° C. The solution was aged for 15 min and the layers separated. The organic layer (volume =300 ml) assayed at 163 mg/ml iodohydrin. Yield=91% (48.9 g present/53.7 g theory).

C. Conversion of AIM Acetonide to Iodohydrin with Iodine

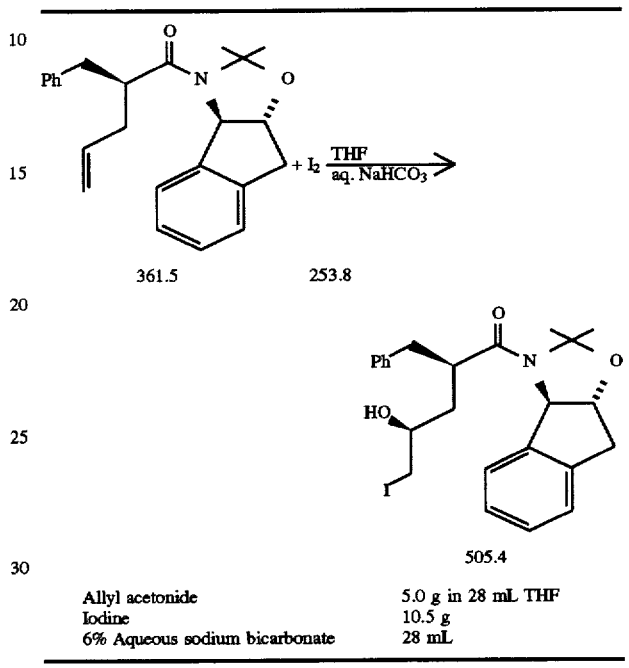

| | |
|---|---|
| Allyl acetonide | 5.0 g in 28 mL THF |
| Iodine | 10.5 g |
| 6% Aqueous sodium bicarbonate | 28 mL |

Allyl acetonide (5.0 g; 13.8 mmols) was dissolved in THF (28 ml) at 18° C., followed by the addition of 6% aq. sodium bicarbonate (28 ml; ca. 20 mmols) and iodine (10.5 g; 41.5 mmols). The reaction mixture was aged at this temperature for 4.5 hrs before being quenched with aq. sodium sulfite (5 g in 20 ml water). The pH was adjusted to 6.7 with solid sodium bicarbonate. The volatiles were removed in vacuo at 25°–27° C. and the residue extracted with IpAc (1×50 ml). LC assay of the organic layer indicates 5.4 g of iodohydrin present (76%).

D. Procedure for the Through Processing of Acetonide to Epoxide with NCS/NaI Iodohydrin Formation Conditions and NaOMe Epoxidation

I. Synthesis of AIM Acetonide

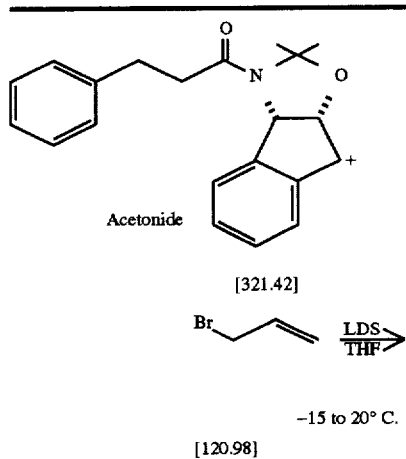

The crystalline acetonide (200 g, 0.622 mol, 99.1 wt. %) is dissolved in 1.25 L sieve dried THF (KF=11 mg/L) under nitrogen atmosphere at 25° C. with mechanical stirring. The resulting KF of the solution at this point is 40 mg/L. The solution is subjected to three alternating vacuum/nitrogen purge cycles to thoroughly degas the solution of dissolved oxygen.

Allyl bromide is added to the THF solution. The resulting KF was 75 mg/L. Typical complete conversion (>99.5 %) has been obtained with pre-LDS solution KF levels of 200 mg/L with the 10% base excess present. The solution was then cooled to −20° C. A THF solution of lithium hexamethyldisilazide (LDS, 1.32M) is added to the allyl bromide/3 solution at such a rate as to maintain the reaction temperature at −20° C. The LDS addition took 30 min. The mixture was aged at −15° to −20° C. and quenched when the conversion was >99%. Analysis of the reaction was carried out by HPLC. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°–15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by $^1$H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86L.

The pH of the mixture after the three aqueous washes was 6.5, 1.3 and 8.5, respectively. HPLC analysis of the mixture at this point indicated 93–94% assay yield for aceotonide. The ratio of allylacetonide/epi-allylacetonide was 96:4 by HPLC (same conditions as above). GC analysis at this point indicated that the hexamethyldisilazane by-product had been completely removed in the workup.

II. Synthesis of Iodohydrin

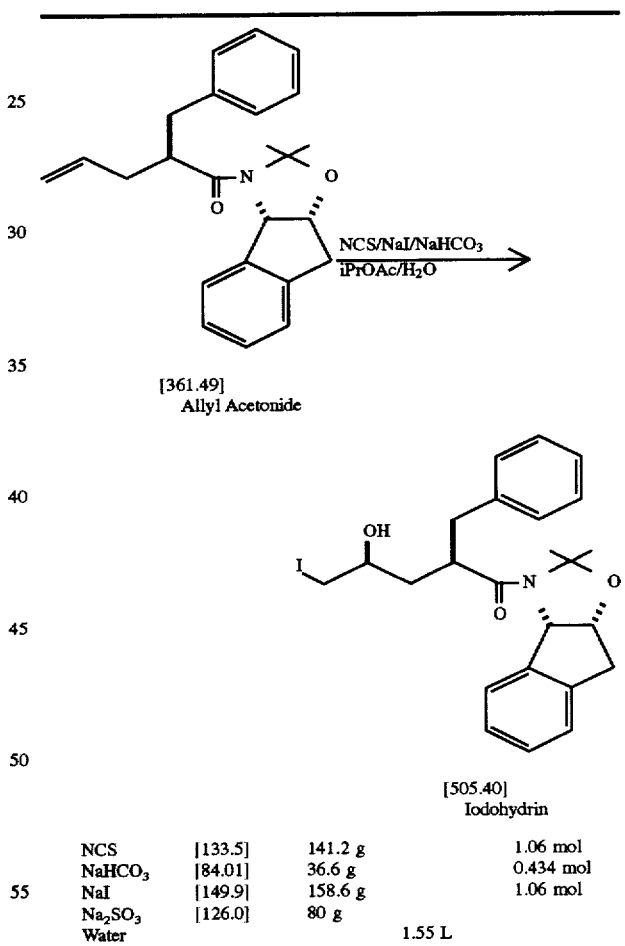

To the allyl acetonide solution in IPAc from the previous step at 25° C. was added a solution of 36.6 g of sodium bicarbonate in 1.03 L of distilled water and the biphasic mixture was cooled to 5° C. Solid N-chlorosuccinimide (141.2 g, 1.06 mol) was added. There was no exotherm after the addition of NCS. To this mixture was added an aqueous solution of sodium iodide (158.6 g, 1.06 mol) while maintaining the reaction mixture at 6°–11° C. The addition took 30 min, and the mixture became dark. The mixture was warmed to 25° C. and aged with vigorous stirring. Progress of the reaction was monitored by HPLC: same system as above, approximate retention times: iodohydrin=8.1 min; allyl acetonide=11.8 min. Analysis of the mixture by HPLC after 2.25 h indicated >99.5 % conversion. The agitation was discontinued and the layers were separated. To the organic phase was added aqueous sodium sulfite (80 g, 0.635 mol in 400 mL) over 10–15 min. The sodium sulfite solution serves to reduce the unreacted electrophilic halogen species. The temperature of the mixture rose from 26°–29° C. after the sodium sulfite addition. The mixture was agitated for 40 min at 25° C. The solution was substantially decolorized after the sulfite wash. The layers were separated; the KF of the organic phase at this point was 25 g/L. The volume of the organic phase was 1.97 L. Quantitative analysis of the mixture by HPLC (same system as above) indicated a 86% overall assay yield of the iodohydrin at this point (corrected for coeluting diastereomers).

III. Synthesis of Epoxide

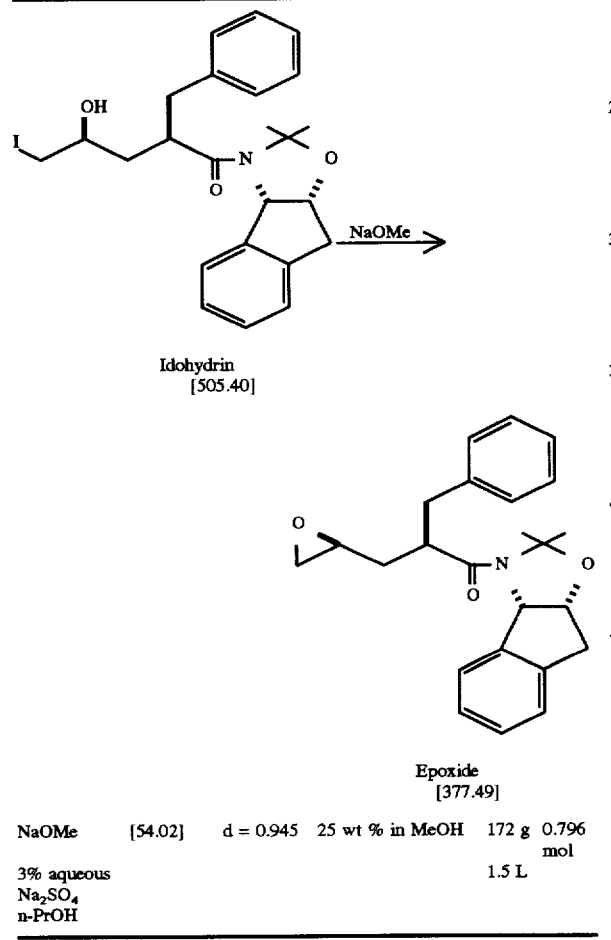

Idohydrin
[505.40]

Epoxide
[377.49]

| NaOMe | [54.02] | d = 0.945 | 25 wt % in MeOH | 172 g | 0.796 mol |
| 3% aqueous Na₂SO₄ | | | | 1.5 L | |
| n-PrOH | | | | | |

The solution of the iodohydrin was concentrated in vacuo (28" Hg) to azeotropically dry the batch. A total of 700 mL of distillate was collected while maintaining a batch temperature of 22°–28° C. The distillate was replaced with 500 mL of IPAc (KF=275 mg/L). The iodohydrin is unstable when heated. The KF of the mixture at this point was 11 g/L. Water levels in excess of KF=18 g/L result in incomplete conversion in the epoxidation reaction due to acceleration of the retrograde reaction. The solution was cooled to 26° C. and 25% NaOMe/MeOH solution (168.1 g) was added over a 10 min period. The temperature dropped to 24° C. after the addition of sodium methoxide. The mixture became darker and a gummy solid briefly formed which redissolved. The mixture was aged for 1 h at 25° C. Analysis of the reaction was carried out by HPLC (same conditions as above), approximate retention times: epoxide =7.1 min, iodohydrin= 8.1 min. HPLC analysis indicated 99% conversion of the iodohydrin to the epoxide. After an additional 40 min, 4.1 g of the sodium methoxide/methanol solution was added. After 20 min, HPLC analysis indicated 99.5% conversion. The reaction was quenched by the addition of 366 mL of water at 25° C. which was then agitated briefly (10 min) and the layers were separated.

The organic phase was washed with 3% aqueous sodium sulfate (2×750 mL). The volume of the organic phase was 1.98 L after the washes. The pH of the three water washes was 10.7, 9.4 and 8.6, respectively. HPLC analysis indicated a 86% overall assay yield of epoxide at this point. The IPAc solution of epoxide was concentrated at reduced pressure (28" Hg) to a volume of about 600 mL while maintaining the batch at 15°–22° C. The solvent was switched to n-PrOH by adding 750 mL n-PrOH while vacuum concentrating to a pot volume of about 500 mL, maintaining the batch at <30° C. Analysis of the solvent composition by ¹H NMR showed <1 mol % IPAc remaining. The thick slurry was cooled to −10° C. over an hour and aged for 45 min. The solids were filtered and washed with 125 mL of cold nPrOH. The product was dried in a vacuum oven at 25° C. to afford 188.5 g of epoxide (98.9 A %, 97.6 wt. %, 79.3% yield overall from acetonide.)

EXAMPLE 4

Preparation of Amide 1

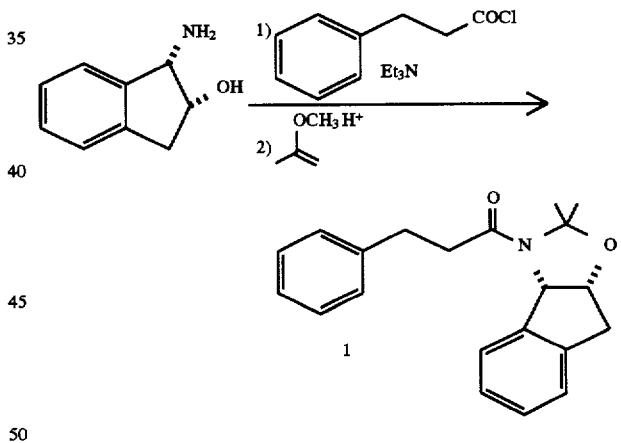

A solution of (-)-cis-1-aminoindan-2-ol (884 g, 5.93 mol) in 17.8 L of dry THF (KF=55 mg/mL) (KF stands for Karl Fisher titration for water) and triethylamine (868 mL, 6.22 mol) in a 50 L round bottom flask equipped with a thermocouple probe, mechanical stirrer, and a nitrogen inlet adapter and bubbler, was cooled to 15° C. Then, 3-phenylpropionyl chloride (1000 g, 5.93 mol) was added over 75 minutes, while the internal temperature between 14°–24° C. with an ice-water cooling batch. After addition, the mixture was aged at 18° to 20° C. for 30 minutes and checked by HPLC analysis for the disappearance of (-)-cis-1-aminoindan-2-ol.

Progress of the reaction is monitored by high performance liquid chromatography (HPLC) analysis: 25 cm Dupont C8-RX column, 60:40 acetonitrile/10 mM (KH₂PO₄/K₂HPO₄), 1.0 mL/min., injection volume=20 mL, detection=200 nm, sample preparation=500×dilution.

Approximate retention times:

| retention time (min.) | identity |
|---|---|
| 6.3 | cis-aminoindanol |

The reaction was treated with pyridinium p-toluenesulfonate (241 g, 0.96 mol, 0.16 equiv.) and stirred for 10 minutes (the pH of the mixture after diluting 1 mL sample with an equal volume of water is between 4.3–4.6). Then, 2-methoxypropene (1.27 L, 13.24 mol, 2.2 equiv.) was added and reaction was heated to 38°–40° C. for 2 h. The reaction mixture was cooled to 20° C. and partitioned with ethyl acetate (12 L) and 5% aqueous $NaHCO_3$ (10 L). The mixture was agitated and the layers were separated. The ethyl acetate extract was washed with 5% aqueous $NaHCO_3$ (10 L) and water (4 L). The ethyl acetate extract was dried by atmospheric distillation and solvent switched to cyclohexane (total volume of ~30 L). At the end of the distillation and concentration (20 volume % of ethyl acetate extraction volume), the hot cyclohexane solution was allowed to slowly cool to 25° C. to crystallize the product. The resulting slurry was further cooled to 10° C. and aged for 1 h. The product was isolated by filtration and the wet cake was washed with cold (10° C.) cyclohexane (2×800 mL). The washed cake was dried under vacuum (26" of Hg) at 40° C. to afford 1.65 kg of acetonide 1 (86.4%, 98 area % by HPLC). $^1H$ NMR (300.13 MHz, $CDCl_3$, major rotamer) δ 7.36–7.14 (m, 9H), 5.03 (d, J=4.4, 1H), 4.66 (m, 1H) 3.15 (m, 2H), 3.06 (br s, 2H), 2.97 (m, 2H), 1.62 (s, 3H), 1.37 (s, 3H); $^{13}C$ NMR (75.5 MHz, $CDCl_3$, major rotamer) $δ_c$ 168.8, 140.9, 140.8, 140.6, 128.6, 128.5, 128.4, 127.1, 126.3, 125.8, 124.1, 96.5, 78.6, 65.9, 38.4, 36.2, 31.9, 26.5, 24.1. Anal. Calcd for $C_{21}H_{23}NO_2$: C, 78.47; H, 7.21; N, 4.36. Found: C, 78.65; H, 7.24; N, 4.40.

EXAMPLE 5

Preparation of Epoxide 3

Tosylate Method

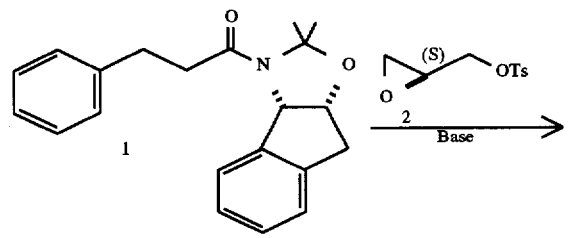

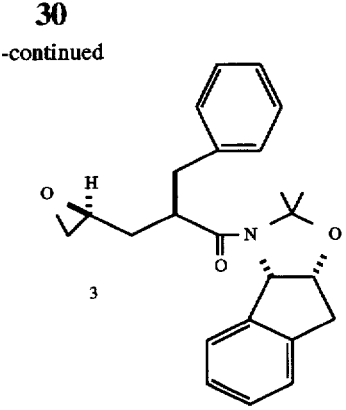

A solution of acetonide 1 (1000 g, 3.11 mol) and 2(S)-glycidyl tosylate 2 (853 g, 3.74 mol, 1.2 equiv.) in 15.6 L of THF (KF=22 mg/mL) in a 50 L 4-neck round bottom flask, equipped with a thermocouple, mechanical stirrer, addition funnel and nitrogen inlet adapter was degassed 3 times via vacuum-nitrogen purge and cooled to –56° C. Then, lithium hexamethyldisilazide $(LiN[(CH_3)_3Si]_2)$(2.6 L, 1.38M, 1.15 equiv.) was added over 2 h, while keeping the internal temperature between –50° to –45° C. The reaction mixture was stirred at –45° to –40° C. for 1 h and then allowed to warm to –25° C. over 1 h. The mixture is stirred between –25° to –22° C. for 4 h (or until the starting acetonide is 3.0 area %).

Progress of the reaction is monitored by HPLC analysis: 25 cm×4.6 nm Zorbax Silica column, 20% ethyl acetate in hexane, 2.0 mL/min, injection volume=20 mL, detection= 254 nm, sample preparation=100×dilution. Approximate retention times:

| retention time (min.) | identity |
|---|---|
| 5.5 | amide 1 |
| 6.5 | glycidyl tosylate 2 |
| 13.5 | epoxide 3 |

The reaction mixture was quenched with DI water (6.7 L) at –15° C. and partitioned with ethyl acetate (10 L). The mixture was agitated and the layers were separated. The ethyl acetate extract was washed with a mixture of 1% aqueous $NaHCO_3$ (5 L) and saturated NaCl (0.5 L). The ethyl acetate extract (28.3 L) was concentrated by vacuum distillation (28" of Hg) and additional ethyl acetate was added to complete the solvent switch to ethyl acetate (final volume=11.7 L). The ethyl acetate concentrate was further solvent switched to MeOH to crystallize the product and concentrated to a final volume of 3.2 L. The residual ethyl acetate solvent was removed by charging 10 L of methanol and collecting 10 L of distillate. The resulting slurry was stirred at 22° C. for 1 h, then cooled to 5° C. and aged for 0.5 h. The product was isolated by filtration and the wet cake was washed with cold methanol (2×250 mL). The washed cake was dried under vacuum (26" of Hg) at 25° C. to afford 727 g of epoxide 3 (61.2%, 98.7 area % of the major epoxide by HPLC): $^{13}C$ NMR (300 MHz, $CDl_3$)δ 171.1, 140.6, 140.5, 139.6, 129.6, 128.8, 128.2, 127.2, 126.8, 125.6, 124.1, 96.8, 79.2, 65.8, 50.0, 48.0, 44.8, 39.2, 37.4, 36.2, 26.6, 24.1.

EXAMPLE 6

Preparation of penultimate 6

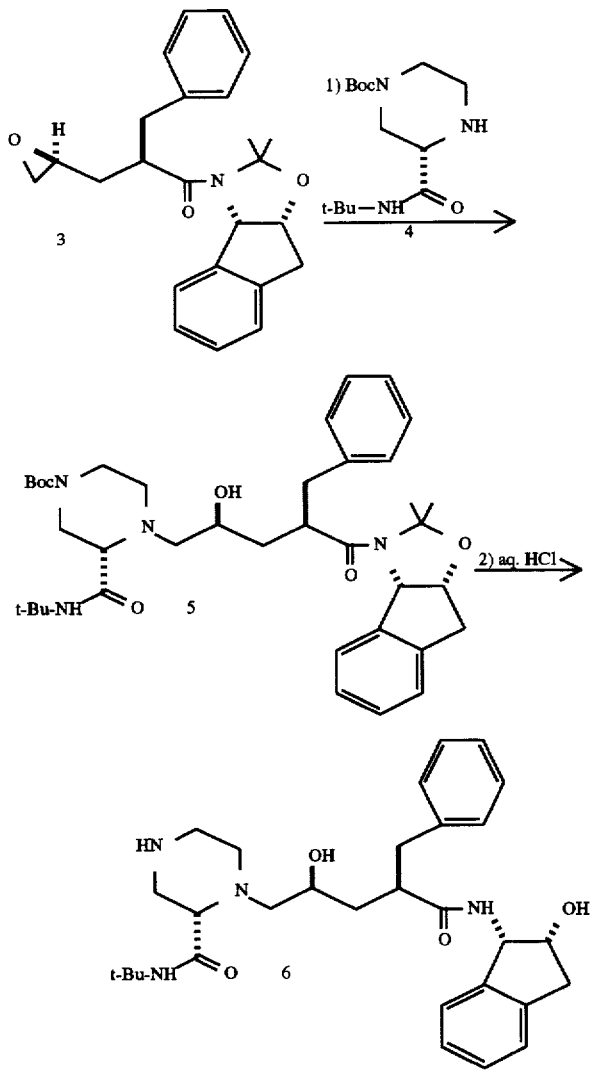

A slurry of the 2(S)-t-butylcarboxamide-4-N-Boc-piperazine 4 (1950 g, 6.83 mol, >99.5% ee) (ee= enantiomeric excess) and the epoxide 3 (2456 g, 97.5:2.5 mixture of 4S/R epoxides, 6.51 mol) in isopropanol (2-propanol, 18.6 L) in a 72 L round bottom flask with four inlets, equipped with a mechanical stirrer, reflux condenser, steam bath, Teflon coated thermocouple and nitrogen inlet, was heated to reflux (internal temperature was 84°–85° C.). After 40 min. a homogeneous solution was obtained. The mixture was heated at reflux for 28 h.

The internal temperature during reflux was 84°–85° C. Progress of the reaction was monitored by HPLC analysis: 25 cm Dupont C8-RX column, 60:40 acetonitrile/10 mM ($KH_2PO_4/K_2HPO_4$), 1.0 mL/min., detection=220 nm, sample preparation=2 μL, reaction mixture diluted to 1 mL in acetonitrile. Approximate retention times:

| retention time (min) | identity |
|---|---|
| 4.8 | piperazine 4 |
| 8.9 | epoxide 3 |
| 15.2 | coupled product 5 |

After 28 h, the remaining epoxide 3 and coupled product 5 (by HPLC analysis) were 1.5 area % and 91–93 area %, respectively. The mixture was cooled to 0° to 5° C. and 20.9 L of 6N HCl was added while keeping the temperature below 15° C. After the addition was complete, the mixture was warmed to 22° C. Evolution of gas is noted at this point (isobutylene). The mixture was aged at 20° to 22° C. for 6 h.

Progress of the reaction was monitored by HPLC analysis: same conditions as above. Approximate retention times:

| retention time (min) | identity |
|---|---|
| 7.0 | cis-aminoindanol |
| 11.9 | penultimate 6 |
| 15.1 | coupled product 5 |

The mixture was cooled to 0° C. and 7.5 L of 50% NaOH was slowly added to adjust the pH of the mixture to pH=11.6, while keeping the temperature less than 25° C. during the addition. The mixture was partitioned with ethyl acetate (40 L) and water (3 L). The mixture was agitated and the layers were separated. The organic phase (60 L) was concentrated under reduced pressure (29" of Hg) and solvent switched to DMF and concentrated to a final volume of 10.5 L (KF=1.8 mg/mL). The HPLC assay yield of 6 in ethyl acetate was 86.5%. The penultimate compound 6 in DMF was directly used in the next step without further purification. For isolated 6: $^{13}C$ NMR (75.4 MHz, $CDCl_3$) δ 175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 7

Preparation of monohydrate of Compound J

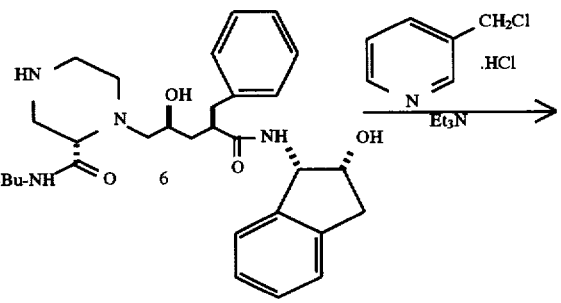

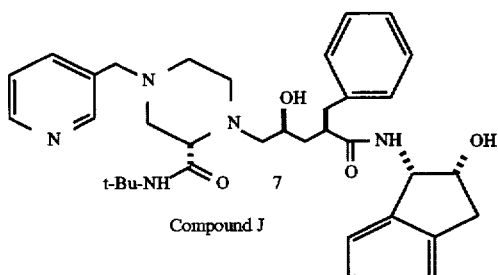

Compound J

EXAMPLE 8

Pyrazine-2-tert-butyl carboxamide 9

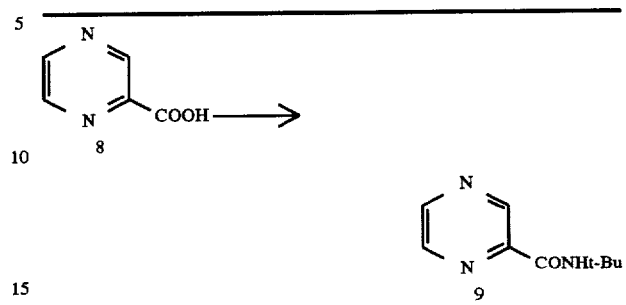

| | |
|---|---|
| 2-Pyrazinecarboxylic acid (8) | 3.35 kg (27 mol) |
| Oxalyl chloride | 3.46 kg (27.2 mol) |
| tert-Butylamine (KF = 460 μg/ml) | 9.36 L (89 mol) |
| EtOAc (KF = 56 μg/ml) | 27 L |
| DMF | 120 mL |
| 1-Propanol | 30 L |

The solution of 6 in DMF (10.5 L, KF=10 mg/mL) from the previous step was charged with 8 L of sieve dried DMF (KF.<30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, 1287 g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 6 |

The mixture was aged at 68° C. until the residual penultimate compound 6 was <0.3 area % by HPLC analysis.

The mixture was stirred at 68° C. for 4 h, then cooled to 25° C. and partitioned with ethyl acetate (80 L) and a mixture of 24 L of saturated aqueous NaHCO₃ and distilled water (14 L). The mixture was agitated at 55° C. and the layers were separated. The ethyl acetate layer was washed three times with water (20 L) at 55° C. The washed ethyl acetate layer is concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

The carboxylic acid 8 was suspended in 27 L of EtOAc and 120 mL of DMF in a 72 L 3-neck flask with mechanical stirring under N₂ and the suspension was cooled to 2° C. The oxalyl chloride was added, maintaining the temperature between 5° and 8° C.

The addition was completed in 5 h. During the exothermic addition CO and CO₂ were evolved. The HCl that was formed remained largely in solution. A precipitate was present which is probably the HCL salt of the pyrazine acid chloride. Assay of the acid chloride formation was carded out by quenching an anhydrous sample of the reaction with t-butylamine. At completion <0.7% of acid 8 remained.

The assay for completion of the acid chloride formation is important because incomplete reaction leads to formation of a bis-tert-butyl oxamide impurity.

The reaction can be monitored by HPLC: 25 cm Dupont Zorbax RXC8 column with 1 mL/min flow and detection at 250 nm; linear gradient from 98% of 0.1% aqueous H₃PO₄ and 2% CH₃CN to 50% aqueous H₃PO₄ and 50% CH₃CN at 30 min. Retention times: acid 8=10.7 min, amide 9=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% NaHCO₃ and 2×2 L of saturated aq. NaCl. The organic phase was treated with 200 g of Darco G60 carbon and filtered through Solka Flok and the cake was washed with 4 L of EtOAc.

Carbon treatment efficiently removed some purple color in the product.

The EtOAc solution of 9 was concentrated at 10 mbar to 25% of the original volume. 30 L of 1-propanol were added, and the distillation was continued until a final volume of 20 L was reached.

At this point, the EtOAc was below the limit of detection in the ¹H NMR (<1%). The internal temperature in this solvent change was <30° C. A 1-propanol/EtOAC solution of 3 was stable to reflux atatmospheric pressure for several days.

Evaporation of an aliquot gave a tan solid m.p 87°–88° C. ¹³C NMR (75 MHz, CDCl₃, ppm) 161.8, 146.8, 145.0, 143.8, 142.1, 51.0, 28.5.

EXAMPLE 9 rac-2-tert-Butyl-carboxamide-piperazine 10

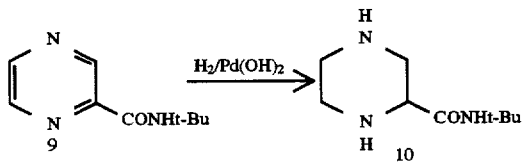

Materials

Pyrazine-2-tert-butylcarboxamide 9 2.4 kg (13.4 mol) in 1-Propanol solution 12 L 20% Pd(OH)₂/C 16 wt. % water 144 g The pyrazine-2-tert-butylcarboxamide 9/1-propanol solution was placed into the 5 gal autoclave. The catalyst was added and the mixture was hydrogenated at 65° C. at 40 psi (3 atm) of H₂.

After 24 h. the reaction had taken up the theoretical amount of hydrogen and GC indicated <1% of 9. The mixture was cooled, purged with N₂ and the catalyst was removed by filtration through Solka Floc. The catalyst was washed with 2 L of warm 1-propanol.

It was found that the use of warm 1-propanol during washing of the filter cake improved filtration and lowered the losses of product on the filter cake.

The reaction was monitored by GC: 30 m Megabore column, from 100° C. to 160° C. at 10° C./min, hold 5 min, then at 10° C./min to 250° C., retention times: 9=7.0 min, 10=9.4 min. The reaction could also be monitored by TLC with EtOAc/MeOH (50:50) as solvent and Ninhydrin as developing agent.

Evaporation of an aliquot indicated that the yield over amidation and hydrogenation is 88% and that the concentration of 10 is 133 g/L.

Evaporation of an aliquot gave 10 as a white solid m.p. 150°–151° C.; ¹³C NMR (75 MHz, D₂O, ppm) 173.5, 59.8, 52.0, 48.7, 45.0, 44.8, 28.7.

EXAMPLE 10

(S)-2-tert-Butyl-carboxamide-piperazine bis (S)-Camphorsulfonic acid salt (S)-11

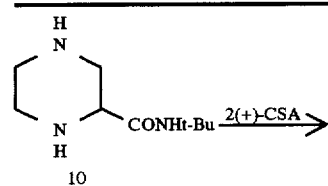

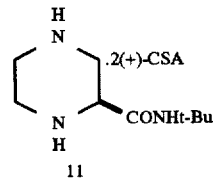

Materials

| | |
|---|---|
| rac-2-tert-Butyl-carboxamide-piperazine 10 in 1-Propanol Solution | 4.10 kg (22.12 mmol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 10 in 1-propanol was charged to a 100 L flask with an attached batch concentrator. The solution was concentrated at 10 mbar and a temperature<25° C. to a volume of ca 12 L.

At this point the product had precipitated from the solution, but went back into a solution when the mixture was heated to 50° C.

Analysis of a homogeneous aliquot indicated that the concentration of 10 was 341 g/L The concentration was determined by HPLC: 25 cm Dupont Zorbax RXC8 column with 1.5 mL/min flow and detection at 210 nm, isocratic (98/2) CH₃CN/0.1% aqueous H₃PO₄. Retention time of 10:2.5 min.

Acetonitrile (39 L) and water (2.4 L) were added to give a clear, slightly brown solution.

Determination of the water content by KF titration and CH₃CN/1-propanol ratio by ¹H NMR integration showed that the CH3CN/1-propanol/H₂O ratio was 26/8/1.6. The concentration in the solution was 72.2 g/L.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21 ° C. over 8 h.

The product precipitated at 62° C. The product was filtered without aging at 21 ° C., and the filter cake was washed with 5 L of the CH₃CN/1-propanol/H₂O 26/8/1.6 solvent mixture. It was dried at 35° C. in the vacuum oven with N2 bleed to give 5.6 Kg (39%) of 11 as a white crystalline solid m.p 288°–290° C. (with decomp.) [α]D²⁵= 18.9° (c=0.37, H₂O). ¹³C NMR (75 MHz, D₂O, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The ee of the material was 95% according to the following chiral HPLC assay: an aliquot of 11 (33 mg) was suspended in 4 mL of EtOH and 1 mL of Et₃N. Boc₂O (11 mg) was added and the reaction mixture was allowed to age for 1h. The solvent was completely removed in vacuo, and the residue was dissolved in ca. 1 mL of EtOAc and filtered through a Pasteur pipet with SiO₂, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 11

(S)-2-tert-Butylcarboxamide-4-tert-butoxycarbonyl-piperazine 4 from salt 11

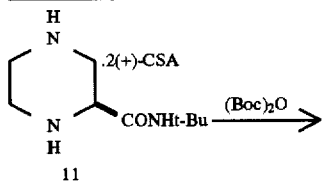

| Materials | |
|---|---|
| (S)-2-tert-Butyl-carboxamide-piperazine Bis(S)-(+)-CSA salt 11, 95% ee | 5.54 Kg (8.53 mol) |
| Di-tert-butyl dicarbonate | 1.86 Kg (8.53 mol) |
| Et₃N | 5.95 L (42.6 mol) |
| EtOH Punctilious 200 proof | 55 L |
| EtOAc | 2 L |

To the (S)-CSA salt 11 in a 100 L 3-neck flask with an addition funnel under N₂ was added EtOH, followed by triethylamine at 25° C. The solid dissolved readily on the addition of the Et₃N. The Boc₂O was dissolved in EtOAc and charged to the addition funnel. The solution of Boc₂O in EtOAc was added at such a rate as to keep the temperature below 25° C. The addition took 3 h. The reaction mixture was aged for 1 h after completion of the addition of the Boc₂O solution.

The reaction can be monitored by HPLC:25 cm Dupont Zorbax RXC8 column with I mL/min flow and detection at 228 nm, isocratic (50/50) CH₃CN/0.1 M KH₂PO₄ adjusted to pH=6.8 with NaOH. Retention time of 4=7.2 min. The chiral assay was carried out using the same system as in the previous step. The reaction could also be monitored by TLC with a 100% EtOAc as the solvent. (R_f=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous Na₂CO₃ solution, 2×10 L Di water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under N₂ bleed to give 1.87 Kg (77%, >99.9 area % by HPLC, R-isomer below level of detection) of 4 as a slightly tan powder. [α]D²⁵=22.0° (c=0.20, MeOH), m.p 107° C.; ¹³C NMR (75 MHz, CDCl₃, ppm) 170.1, 154.5, 79.8, 58.7, 50.6, 46.6, 43.6, 43.4, 28.6, 28.3.

While the foregoing specification teaches the principles of the present invention, with examples provided for the purpose of illustration, it will be understood that the practice of the invention encompasses all of the usual variations, adaptations, modifications, deletions or additions of procedures and protocols described herein, as come within the scope of the following claims and it equivalents.

What is claimed is:

1. A process of synthesizing the epoxide of formula I,

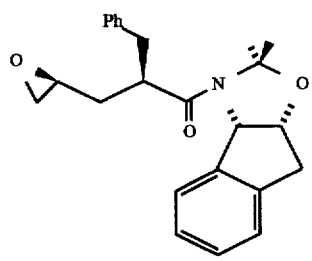

comprising the steps of:

(a) contacting one equivalent of the allyl acetonide of formula II,

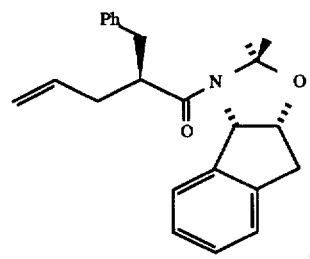

with about one to two equivalents of a halogenating agent in solvent mixed with aqueous weak base, at a temperature range between about −40° C. and about 100° C., to form the halohydrin of formula III,

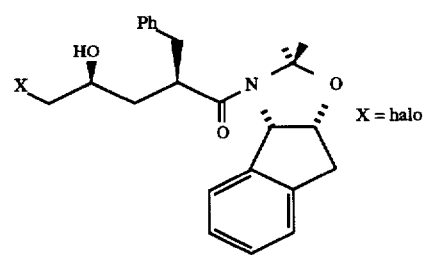

wherein the halogenating agent is selected from N-iodosuccinimide, N,bromosuccinimide in combination with an iodide salt, or N-chlorosuccinimide in combination with an iodide salt, 1,3-dichloro-5,5-dimethylhydantoin with an iodide salt, or iodine; said weak base is selected from sodium bicarbonate, calcium carbonate, magnesium hydroxide, basic alumina, neutral alumina, sodium acetate, dibasic sodium phosphate, dibasic potassium phosphate, potassium fluoride, or water in common organic solvents compatible with the reaction conditions selected from ethers, aromatic chlorinated hydrocarbons, esters, alcohols, MeCN, DMF, DMPU or ketones; and (b) adding base in solvent or solvents to elicit formation of the epoxide of formula I, wherein the base is selected from the group consisting of hydroxides of lithium, sodium, potassium, magnesium, calcium, or tetraalkylammonium and alkoxides selected from the group consisting of lithium, sodium, potassium, magnesium, and tetraalkylammonium methoxide, ethoxide, n- and iso-propoxide, n-, iso-, sec-, and tert-butoxide.

2. The process of claim 1 further comprising reacting one equivalent of an acetonide

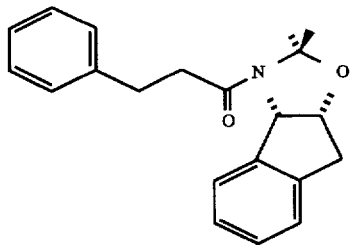

with about one equivalent of allylhalide in strong base, to give the allyl acetonide of formula II,

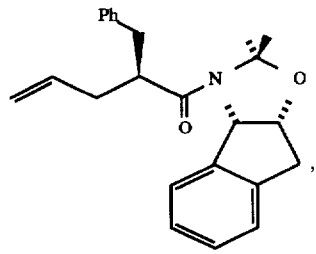

wherein the strong base is selected from amide bases selected from the group consisting of lithium, sodium, potassium and magnesium salts of amines, metal alkyls or aryl lithiums.

3. The process of claim 1, for synthesizing the epoxide of formula I,

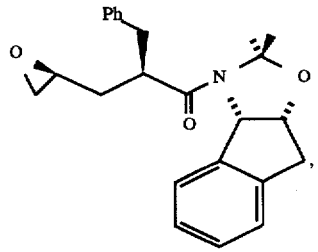

comprising the steps of:
(a) contacting one equivalent of the allyl acetonide of formula II,

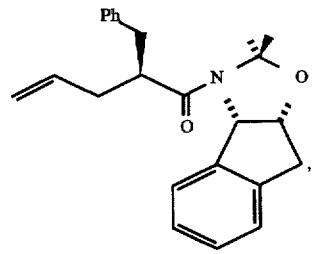

with about one to two equivalents of a halogenating agent, in solvent mixed with aqueous weak base, at a temperature range of between about −40° C. and about 100° C., to form the halohydrin of formula III,

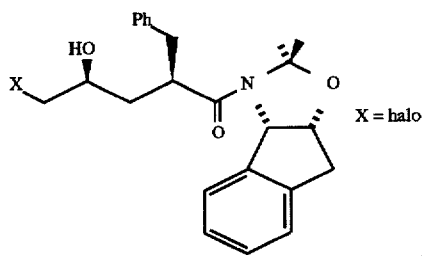

said halogenating agent selected from the group consisting of iodine, N-iodosuccinimide, N-bromosuccinimide, N-chlorosuccinimide or 1,3-dichloro-5,5-dimethylhydantoin, the last three of which may be combined with an iodide IO salt, said solvent selected from the group consisting of dichloromethane, IPAC, THF, EtOAc, DME, and MTBE, said weak base selected from basic alumina or sodium bicarbonate, and (b) adding base in water to elicit formation of the epoxide of formula I, said base selected from the group consisting of lithium hydroxide, sodium hydroxide, potassium hydroxide, tetralkylammonium hydroxide; any $C_{1-4}$ alkoxide of lithium, sodium or potassium; and DIEA.

4. The process of claim 2, for synthesizing the epoxide of formula I,

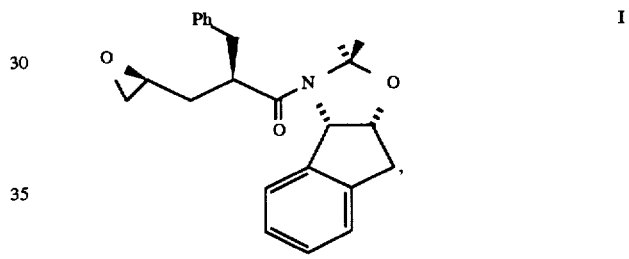

comprising the steps of:
(a) reacting one equivalent of the acetonide

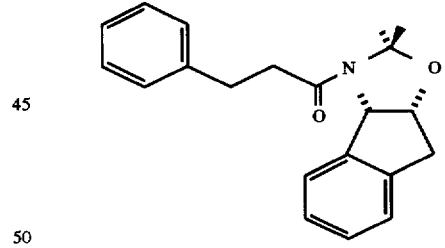

with about one equivalent of allylhalide in strong base, said allyl halide selected from allyl chloride, allyl bromide and allyl iodide, to give the allyl acetonide of formula II,

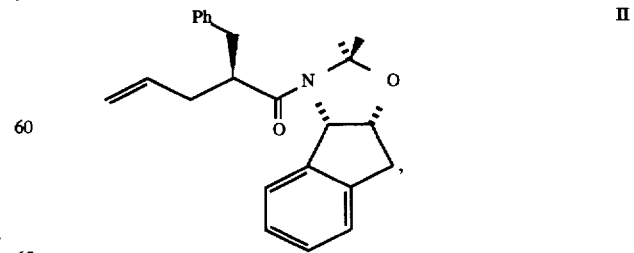

(b) mixing thereto about one to two equivalents of a halogenating agent in solvent mixed with aqueous weak base, at a temperature range of between about −40° C. and about 100° C., to form the halohydrin of formula III,

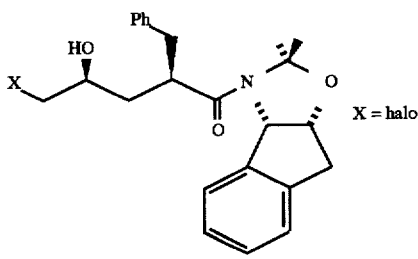

said halogenating agent selected from the group consisting of iodine, N-iodosuccinimide, N-bromosuccinimide, N-chlorosuccinimide or 1,3-dichloro-5,5-dimethylhydantoin, the last three of which may be combined with an iodide salt, said solvent selected from the group consisting of dichloromethane, IPAC, THF, EtOAc, DME, and MTBE, said weak base selected from basic alumina or sodium bicarbonate, and (c) adding base in water to elicit formation of the epoxide of formula I, said base selected from the group consisting of lithium hydroxide, sodium hydroxide, potassium hydroxide, tetralkylammonium hydroxide; any $C_{1-4}$ alkoxide of lithium, sodium or potassium; and DIEA.

5. A process of synthesizing the epoxide of formula I,

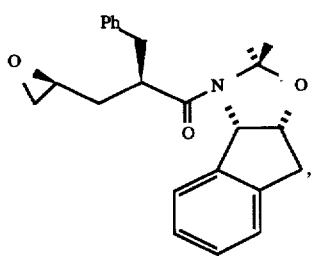

comprising the steps of:

(a) contacting one equivalent of the allyl acetonide of formula II,

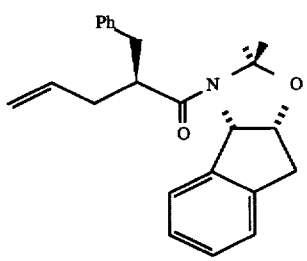

said allyl acetonide dissolved in isopropyl acetate, with about one to two equivalents of N-iodosuccinimide in about 0.5M aqueous sodium bicarbonate, at room temperature, to form the iodohydrin of formula III, and

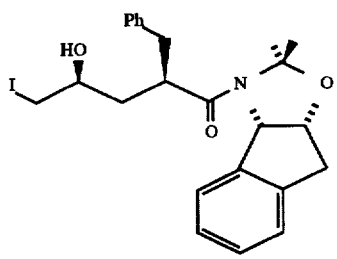

(b) adding alkali hydoxide in water to elicit formation of the epoxide of formula I.

6. A process of synthesizing the epoxide of formula I,

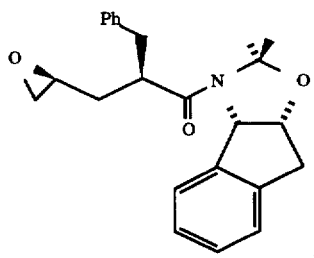

comprising the steps of:

(a) reacting one equivalent of the acetonide

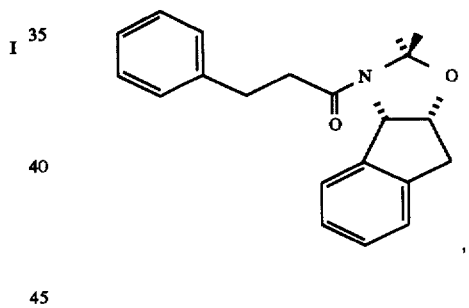

said acetonide dissolved in ethereal solvent, with about one equivalent of allylbromide and about one equivalent of about 1.0–2.0 M lithiumhexamethyldisilazide (in ethereal solvent), to give the allyl acetonide of formula II,

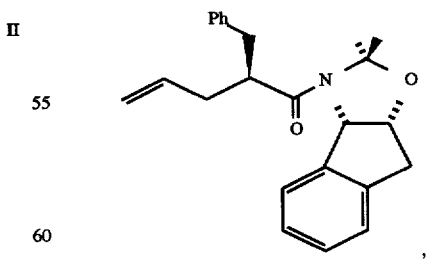

(b) mixing thereto about one to two equivalents of N-iodosuccinimide in about 0.5M aqueous sodium bicarbonate, at room temperature, to form the iodohydrin of formula III, and

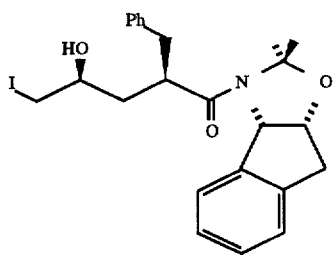

(c) adding alkali hydroxide in water to elicit formation of the epoxide of formula I.

7. The compound

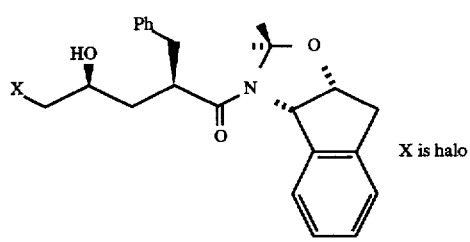

X is halo

8. A process of synthesizing the epoxide of formula I,

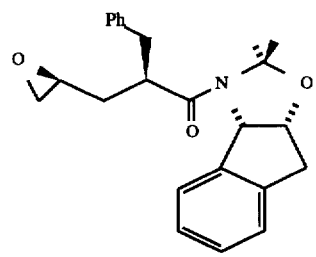

comprising the steps of:

(a) contacting one equivalent of the allyl acetonide of formula II,

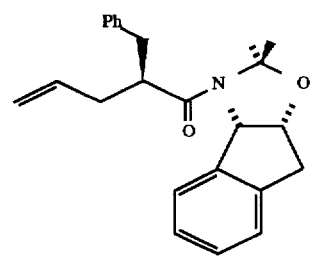

said allyl acetonide dissolved in isopropyl acetate, with aqueous sodium bicarbonate solution and between about 0.5 and about 1.0 equivalents of 1,3-dichloro-5,5-dimethylhydantoin;

(b) cooling the resulting mixture to between about 5° C. and about 10° C.;

(c) adding thereto excess aqueous sodium iodide, warming the reaction mixture to between about 21° C. and about 25° C., and thereafter aging the reaction mixture for between about 1 hour and about 8 hours;

(d) quenching by adding aqueous sodium sulfite, to form the iodohydrin of formula III, and

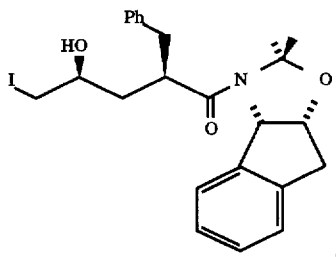

(e) adding sodium methoxide in methanol to elicit formation of the epoxide of formula I.

9. A process of synthesizing the epoxide of formula I,

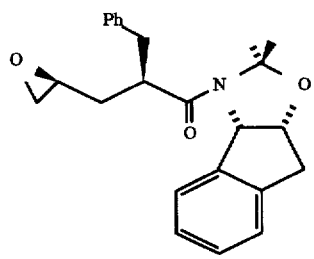

comprising the steps of:

(a) reacting one equivalent of the acetonide

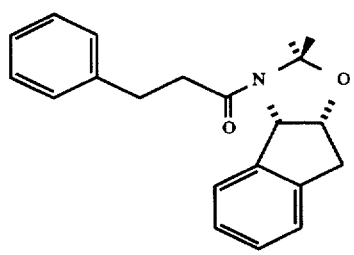

said acetonide dissolved in ethereal solvent, with about one equivalent of allylbromide and about one equivalent of about 1.0–2.0M lithiumhexamethyldisilazide (in ethereal solvent), at a temperature of between about −10° C. and about −20° C., to give the allyl acetonide of formula II,

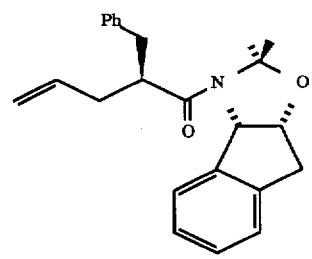

(b) quenching with citric acid;

(c) contacting the allyl acetonide product of step (b), said allyl acetonide dissolved in isopropyl acetate, with aqueous sodium bicarbonate solution and between about 0.5 and about 1.0 equivalents of 1,3-dichloro-5,5-dimethylhydantoin;

(d) cooling the resulting mixture to between about 5° C. and about 10° C.;

(e) adding thereto excess aqueous sodium iodide, warming the reaction mixture to between about 21° C. and about 25° C., and aging between about 1 hour and about 8 hours;

(f) quenching by adding aqueous sodium sulfite; to form the iodohydrin of formula III, and

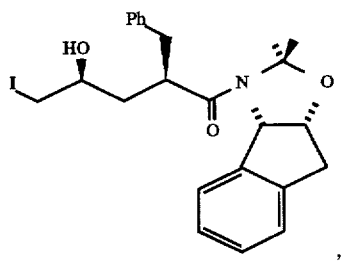

(g) adding sodium methoxide in methanol to elicit formation of the epoxide of formula I.

10. A process of synthesizing the epoxide of formula I,

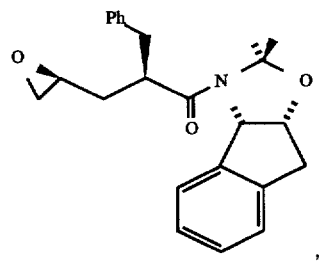

comprising the steps of:

(a) contacting one equivalent of the allyl acetonide of formula II,

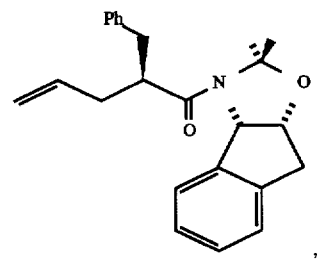

said allyl acetonide dissolved in THF, with aqueous sodium bicarbonate solution and excess iodine;

(b) aging the resulting mixture for between about 3 hours and about 8 hours;

(c) quenching by adding aqueous sodium sulfite, to give

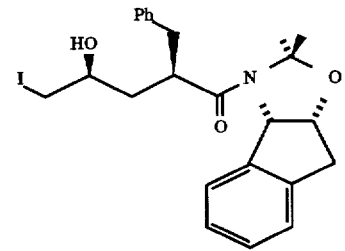

(d) adding sodium methoxide in methanol to elicit formation of the epoxide of formula I.

11. A process of synthesizing the epoxide of formula I,

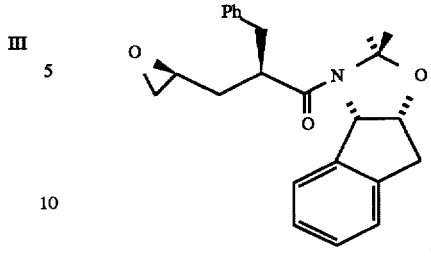

comprising the steps of:

(a) reacting one equivalent of the acetonide

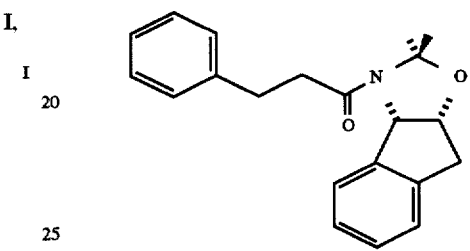

said acetonide dissolved in ethereal solvent, with about one equivalent of allylbromide and about one equivalent of about 1.0–2.0M lithiumhexamethyldisilazide (in ethereal solvent), at a temperature of between about −10° C. and about −20° C., to give the allyl acetonide of formula II,

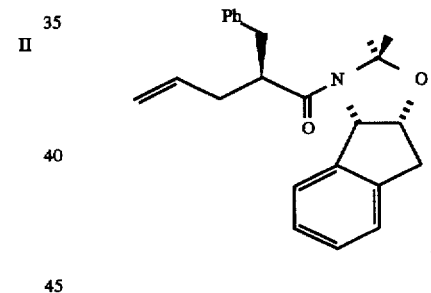

(b) quenching with citric acid;

(c) contacting the allyl acetonide product of step (b), said allyl acetonide dissolved in THF, with aqueous sodium bicarbonate solution and excess iodine;

(d) aging the resulting mixture for between about hours and about 3 hours;

(e) quenching by adding aqueous sodium sulfite, to give

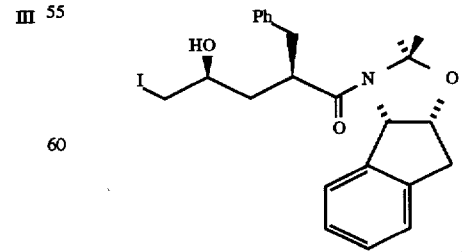

(f) adding sodium methoxide in methanol to elicit formation of the epoxide of formula I.

12. A process of synthesizing the epoxide of formula I,

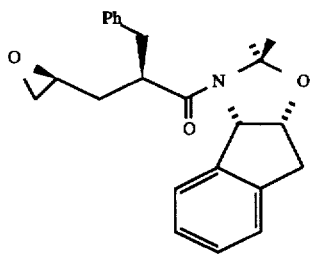

comprising the steps of:

(a) contacting one equivalent of the allyl acetonide of formula II,

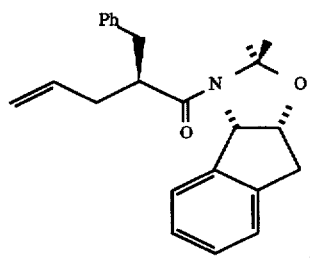

said allyl acetonide dissolved in isopropyl acetate, with aqueous sodium bicarbonate solution and between about 1.0 and about 2.0 equivalents of N-chlorosuccinimide;

(b) cooling the resulting mixture to between about 5° C. and about 10° C.;

(c) adding thereto excess aqueous sodium iodide, warming the reaction mixture to between about 21° C. and about 25° C., and thereafter aging the reaction mixture for between about 1 hour and about 8 hours;

(d) quenching by adding aqueous sodium sulfite, to form the iodohydrin of formula III, and

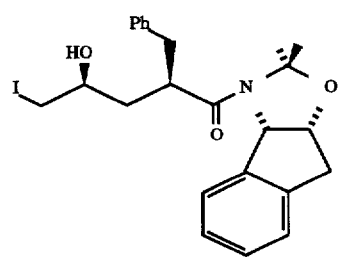

(e) adding sodium methoxide in methanol to elicit formation of the epoxide of formula I.

13. A process of synthesizing the epoxide of formula I,

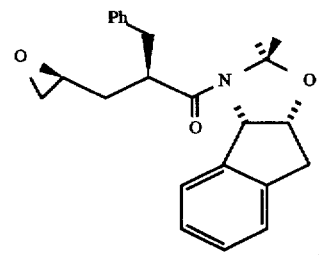

comprising the steps of:

(a) reacting one equivalent of the acetonide

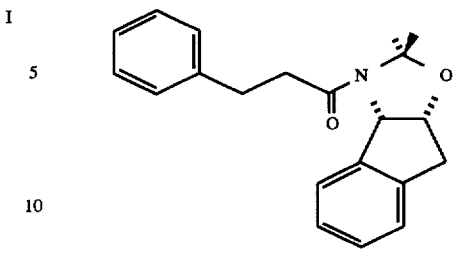

said acetonide dissolved in ethereal solvent, with about one equivalent of allylbromide and about one equivalent of about 1.0–2.0M lithiumhexamethyldisilazide (in ethereal solvent), at a temperature of between about −10° C. and about −20° C., to give the allyl acetonide of formula II,

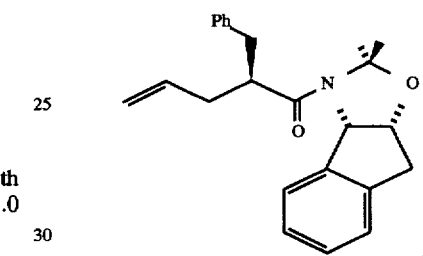

(b) quenching with citric acid;

(c) contacting the allyl acetonide product of step (b), said allyl acetonide dissolved in isopropyl acetate, with aqueous sodium bicarbonate solution and between about 1.0 and about 2.0 equivalents of N-chlorosuccinimide;

(d) cooling the resulting mixture to between about 5° C. and about 10° C.;

(e) adding thereto excess aqueous sodium iodide, warming the reaction mixture to between about 21° C. and about 25° C., and aging between about 1 hour and about 8 hours;

(f) quenching by adding aqueous sodium sulfite; to form the iodohydrin of formula III, and

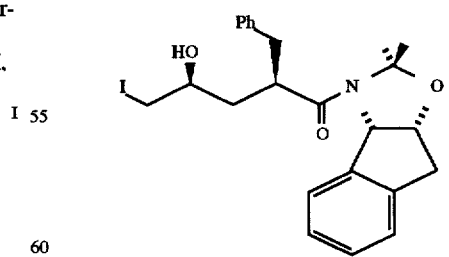

(g) adding sodium methoxide in methanol to elicit formation of the epoxide of formula I.

* * * * *